(12) United States Patent
Tajima et al.

(10) Patent No.: US 8,420,379 B2
(45) Date of Patent: Apr. 16, 2013

(54) MATERIAL FOR CAPTURING MICROBES, DEVICE FOR CAPTURING MICROBES, METHOD OF CAPTURING MICROBES, AND METHOD OF PRODUCING MATERIAL FOR CAPTURING MICROBES

(75) Inventors: Hideji Tajima, Matsudo (JP); Tomoyuki Hatano, Matsudo (JP); Ryouji Karinaga, Matsudo (JP); Madoka Shishido, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 271 days.

(21) Appl. No.: 12/812,290

(22) PCT Filed: Jan. 9, 2009

(86) PCT No.: PCT/JP2009/050223
§ 371 (c)(1),
(2), (4) Date: Sep. 24, 2010

(87) PCT Pub. No.: WO2009/088076
PCT Pub. Date: Jul. 16, 2009

(65) Prior Publication Data
US 2011/0003367 A1 Jan. 6, 2011

(30) Foreign Application Priority Data
Jan. 10, 2008 (JP) .................. 2008-003208

(51) Int. Cl.
*C12M 1/12* (2006.01)
*C12N 1/10* (2006.01)
*C12N 1/14* (2006.01)
*C12N 1/20* (2006.01)

(52) U.S. Cl.
USPC ............. 435/283.1; 435/252.1; 435/254.1; 435/258.1

(58) Field of Classification Search ............. 435/252.1, 435/254.1, 258.1, 283.1
See application file for complete search history.

(56) References Cited

U.S. PATENT DOCUMENTS
4,952,506 A    8/1990    Byers et al.

FOREIGN PATENT DOCUMENTS

| | | |
|---|---|---|
| CA | 2049458 | 8/1990 |
| JP | 52-96778 A | 8/1977 |
| JP | 62-269691 A | 11/1987 |
| JP | 63-031505 A | 2/1988 |
| JP | 63-074991 A | 4/1988 |
| JP | 2000-228924 A | 8/2000 |
| WO | WO 2006/039455 | 4/2006 |

OTHER PUBLICATIONS

International Search Report, mailed Apr. 14, 2009, by the ISA/JP, regarding PCT International Application No. PCT/JP2009/050223.
Written Opinion, mailed Apr. 14, 2009, by the ISA/JP, regarding PCT International Application No. PCT/JP2009/050223.
International Preliminary Report on Patentability, issued Apr. 7, 2010, by the IPEA/JP, regarding PCT International Application No. PCT/JP2009/050223.

*Primary Examiner* — Herbert J Lilling
(74) *Attorney, Agent, or Firm* — Haynes and Boone, LLP

(57) ABSTRACT

The invention relates to a material for capturing microbes or the like, a device for capturing microbes or the like, a method of capturing microbes or the like, and a method of producing a material for capturing microbes or the like, and has an object of using a pulverizable resin whereby a minor amount of microbes or the like contained in a large amount of a liquid, or microbes or the like contained in a small amount of a liquid can be captured efficiently, quickly, labor-savingly, and reliably. Disclosed is: a material for capturing microbes or the like, which comprises irregular-shaped powdery grains made of a pulverizable adsorbent resin and distributed in a predetermined grain size range, and which can adsorb or bond to a target such as a microbe contained in a liquid; a device for capturing microbes or the like; and a method of capturing microbes or the like.

2 Claims, 14 Drawing Sheets

Fig.2
(1) 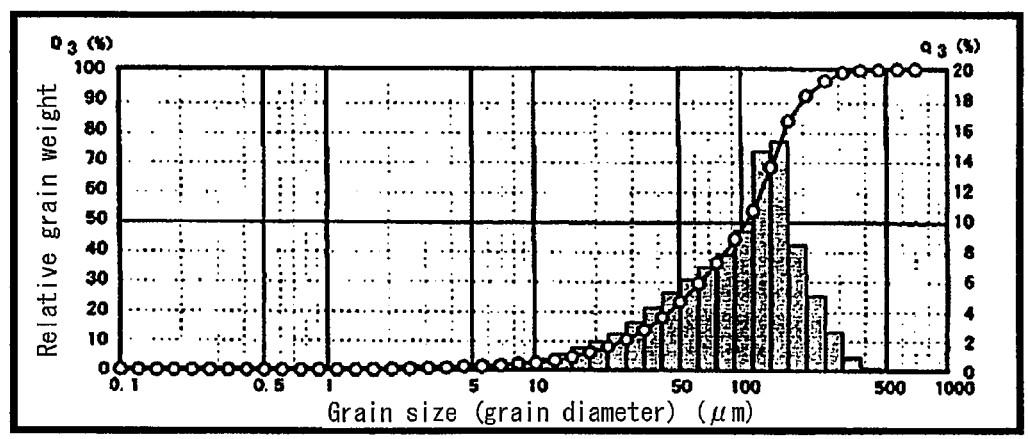
(2) 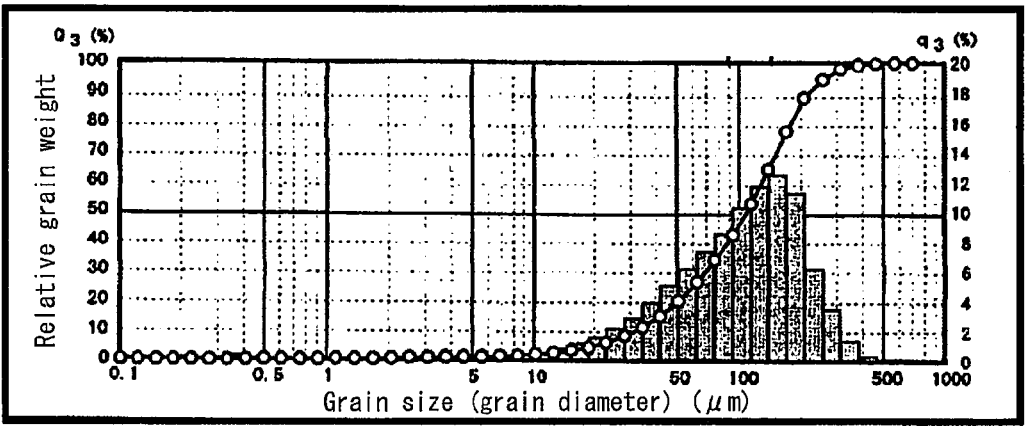
(3) 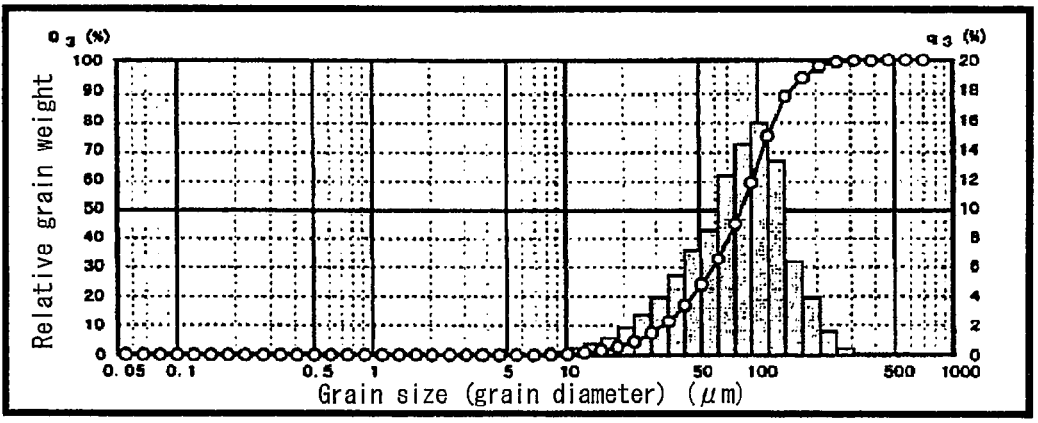

Fig.4
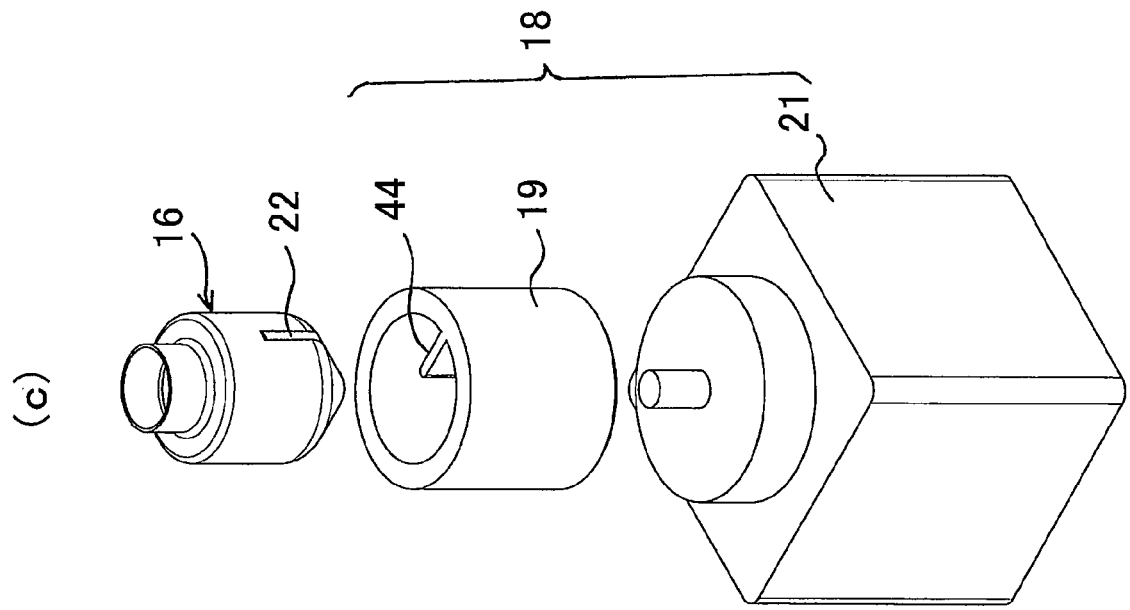
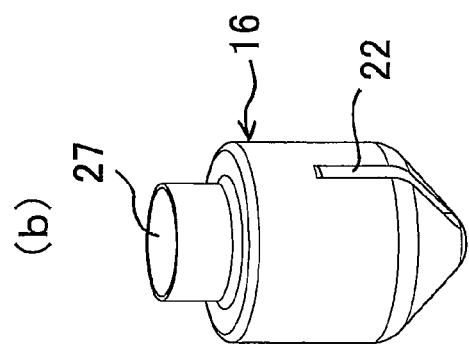
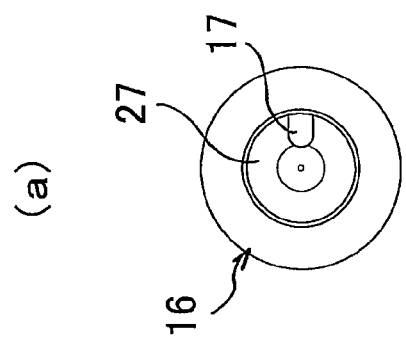

Fig.8

| Concentration method | Water in heat storage tank | Concentration factor | Number of colonies (cfu) | Initial biomass concentration (cfu/100mL) |
|---|---|---|---|---|
| Cooling centrifuging and concentration method | Water in heat storage tank A | x100 | 30 | $3.0 \times 10^2$ |
| Particle concentration method | Water in heat storage tank A | x10000 | 1400 | $1.4 \times 10^2$ |
| Cooling centrifuging and concentration method | Water in heat storage tank B | x100 | 30 | $3.0 \times 10^2$ |
| Particle concentration method | Water in heat storage tank B | x10000 | 2370 | $2.7 \times 10^2$ |

Fig.10
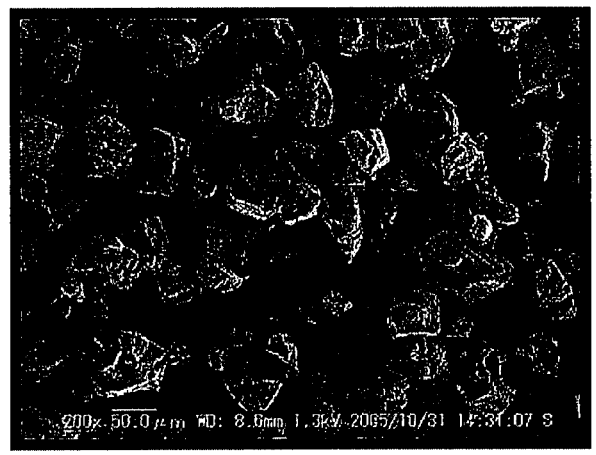
(a)
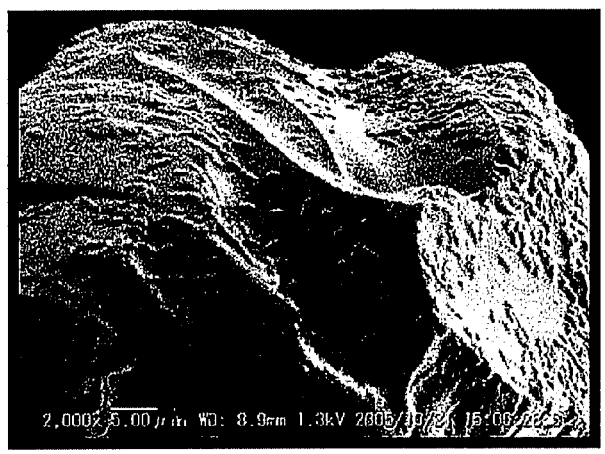
(b)
(c)

(a)

(b)

| | No. | Storage | Storage solution | 0 day | 2 days | 5 days | 7 days | 10 days |
|---|---|---|---|---|---|---|---|---|
| ■ | 1 | 4°C | Saline | 115 | 84 | 66 | 27 | 38 |
| ○ | 2 | 37°C | Saline | 991 | 0 | 0 | 0 | 0 |
| ● | 3 | 4°C | Saline + grains | 214 | 128 | 161 | 138 | 169 |
| ▲ | 4 | 37°C | Saline + grains | 599 | 16 | 0 | 0 | 0 |

| Sample | Number of colonies | Initial concentration cfu/100mL |
|---|---|---|
| Water YJ in heat storage tank | 30 | $3.0 \times 10^2$ |
| Water YJ in heat storage tank added with culture of bacteria | 93 | $9.3 \times 10^2$ |

(b)

| Sample | Number of colonies | Adsorption rate |
|---|---|---|
| Water YJ in heat storage tank | 13 | 57% |
| Water YJ in heat storage tank added with culture of bacteria | 45 | 52% |

(c)

| Place | Device and method for capturing microbes or the like | | | Cooling centrifuging/ concentration method according to Guidelines Culture (cfu/100mL) |
| | Immuno-chromatography | Culture (cfu/100mL) | PCR | |
|---|---|---|---|---|
| SY | Positive | $10^4$ or more | Positive | $1 \times 10^4$ |
| YJ | Negative | $1.4 \times 10^2$ | Negative | $3.0 \times 10^2$ |
| YA | Negative | $2.7 \times 10^2$ | Negative | $3.0 \times 10^2$ |
| CK | Positive | $7.3 \times 10^2$ | Positive | $8.0 \times 10^2$ |

|  | cfu/plate | $10^3$cfu/L |
|---|---|---|
| Initial amount | 129 | 12.9 |
| speed 1, 1 flow | 46 | 4.6 |
| speed 1, 2 cycles | 33 | 3.3 |
| speed 1, 4 cycles | 0 | 0 |
| speed 3, 1 flow | 22 | 2.2 |
| speed 3, 2 cycles | 39 | 3.9 |
| speed 3, 4 cycles | 20 | 2.0 |

× 100 concentration (b)

|  | One flow | Two cycles | Four cycles |
|---|---|---|---|
| Speed 1 | 7 minites<br>64% | 14 minutes<br>74% | 28 minutes<br>100% |
| Speed 3 | 5.5 minites<br>83% | 11minutes<br>70% | 22 minutes<br>85% |

Fig.14

| | Place | No. | Concentration method | HCl treatment | Concentration rate | Eluate dilution rate | Number of colonies (cfu) | Converted to initial concentration (cfu/100mL) |
|---|---|---|---|---|---|---|---|---|
| for outdoor use | YJ | 0 | Centrifugal | Yes | x100 | x1 | 30 | $3.0 \times 10^2$ |
| | | 1 | Particle | Yes | x10000 | x10 | 140 (3) | $1.4 \times 10^2$ |
| | YA | 0 | Centrifugal | Yes | x100 | x1 | 30 | $3.0 \times 10^2$ |
| | | 1 | Particle | Yes | x10000 | x10 | 237 | $2.4 \times 10^2$ |
| for indoor use | CK1 | 0 | Centrifugal | Yes | x100 | x1 | 8 | $8.0 \times 10^2$ |
| | | 1 | Particle | Yes | x1000 | x1 | 56 | $5.6 \times 10^2$ |
| | | 2 | Particle | Yes | x1000 | x1 | 31 | $3.1 \times 10^2$ |
| | | 3 | Particle | No | x1000 | x1 | 54 | $5.4 \times 10^2$ |
| | CK2 | 0 | Centrifugal | Yes | x100 | x1 | 8 | $8.0 \times 10^2$ |
| | | 1 | Particle | Yes | x1000 | x1 | 21 (2) | $2.1 \times 10^2$ |
| | | 2 | Particle | Yes | x1000 | x1 | 22 | $2.2 \times 10^2$ |
| | | 3 | Particle | No | x1000 | x1 | 26 | $2.6 \times 10^2$ |
| | CK3 | 0 | Centrifugal | Yes | x100 | x1 | 217 | $2.2 \times 10^4$ |
| | | 1 | Particle | No | x1000 | x10 | 310 | $3.1 \times 10^4$ |
| | | 2 | Particle | No | x1000 | x10 | 210 | $2.1 \times 10^4$ |
| | | 3 | Particle | No | x1000 | x10 | 339 | $3.4 \times 10^4$ |
| | | 4 | Particle | No | x1000 | x10 | 312 (3) | $3.1 \times 10^4$ |

MATERIAL FOR CAPTURING MICROBES, DEVICE FOR CAPTURING MICROBES, METHOD OF CAPTURING MICROBES, AND METHOD OF PRODUCING MATERIAL FOR CAPTURING MICROBES

CROSS REFERENCE

This application is a United States national phase application of co-pending international patent application number PCT/JP2009/050223, filed Jan. 9, 2009, which claims priority to Japanese patent application number 2008-003208, filed Jan. 10, 2008, the disclosures of which are incorporated herein by reference.

TECHNICAL FIELD

The present invention relates to a material for capturing microbes or the like, a device for capturing microbes or the like, a method of capturing microbes or the like, and a method of producing a material for capturing microbes or the like. The present invention can be used in various fields, in particular, the industrial field, the medical field, the agricultural field, the scientific field, and the drug formulation field.

BACKGROUND ART

Recently, in hospitals or the like, there is an increased need for performing various treatments such as separation, extraction, inspection, and measurement of minute substances such as bacteria (for example, protozoa, and bacteria dissolved in water, such as colon *bacillus* such as O157 and O26, *Legionella* bacteria, *cryptosporidium* bacteria, *salmonella*, *dysentery bacillus*, and *Campylobacter* bacteria).

Particularly, reports of accidents and cases of diseases due to *Legionella* bacteria have been increasing rapidly. Legionnaires' disease was specified as a category 4 infection by the "Law Concerning Prevention of Infections and Medical Care for Patients of Infections" (new law for infection control) in December 1998, and has a risk of death for aged people and people in an immunological deficiency state or in a state with resisting power being weakened. Therefore, investigation into the cause thereof, and stable detection and rapid detection of *Legionella* bacteria have been desired.

The microbes such as bacteria are generally obtained in a condition where a minor amount of microbes are suspended in a large amount (for example, from about 50 mL to about 10 L) of liquid (for example, blood, juice, feces, or sewage). Various treatments such as culturing and amplification of the microbes and PCR for detecting O antigens or Verotoxin (VT) genes need to be performed in a state with the concentration of the microbes being increased.

Regarding Legionnaires' disease, for example, according to "New Guidelines for Prevention of Legionnaires' Disease", chlorination needs to be performed immediately, when an inspection result is 1 cfu/100 ml (cfu: colony forming unit) in an inspection of environmental water in a bath or the like, which a human body directly touches, or when an inspection result is 10 cfu/100 ml in an inspection of environmental water in a cooling tower or a heat storage tank. In order to detect the borderline, enrichment of *Legionella* bacteria from a large amount of samples such as several hundred milliliters is required.

Conventionally, therefore, separation and extraction have been performed by causing a large amount (for example, more than 1 liter) of suspension in which the microbes are suspended, to pass through a barrier filter or sterilization filter, or by centrifugal separation, or by culturing in a medium. Generally, however, the suspension contains a large number of impurities other than the target. Because there is such cloudiness and contamination in the suspension, when the barrier filter or sterilization filter using a pore size smaller than the biomass is a membrane filter or the like, inefficiency has been frequently pointed out, and there is a disadvantage in that these filters are blocked or undesired substances are collected. Moreover, when centrifugal separation is used, it is normal that centrifugal separation is performed for 10 minutes at a speed of 11000 rpm, for example, by obtaining 1 mL of a sample in a tube, and it is difficult to handle a large amount of liquid of more than 1 liter at a time in view of equipment size. Thus, conventionally, it has been difficult to separate a target from a large volume of suspension, and time and labor are required.

Moreover, taking into consideration the case where substances such as bacteria that affect living things such as humans are handled, an apparatus has been desired that can automatically perform treatment without the need of human operation, portions in contact with the suspension can be replaced without the need of washing, and it can be used efficiently and reliably.

To capture microbes or the like such as bacteria, it is known that capturing efficiency can be increased by using a capturing material of an appropriate size corresponding to the size of the bacteria.

DISCLOSURE OF THE INVENTION

Problems to be Solved by the Invention

It is therefore a first object of the present invention to provide a material for capturing microbes or the like, a device for capturing microbes or the like, a method of capturing microbes or the like, and a method of producing the material for capturing microbes or the like, whereby a minor amount of microbes or the like contained in a large amount (for example, from about 50 mL to about 10 L) of a liquid, or microbes or the like contained in a small amount (for example, less than 50 mL) of a liquid can be captured efficiently, quickly, labor-savingly, and reliably.

It is a second object of the present invention to provide a material for capturing microbes or the like, a device for capturing microbes or the like, a method of capturing microbes or the like, and a method of producing the material for capturing microbes or the like, in which concentration, separation, and extraction is not influenced by the presence of impurities other than a target contained in the liquid.

It is a third object of the present invention to provide a material for capturing microbes or the like, a device for capturing microbes or the like, a method of capturing microbes or the like, and a method of producing the material for capturing microbes or the like, which can prevent cross-contamination, can be produced at low cost, and can be handled easily, by using a simple mechanism and a low-cost material, and by having a structure whereby parts in contact with a suspension, such as a container or disposable tip can be replaced.

It is a fourth object of the present invention to provide a material for capturing microbes or the like, a device for capturing microbes or the like, a method of capturing microbes or the like, and a method of producing the material for capturing microbes or the like, suitable for automated treatment and consistent treatment without the need of human operation.

It is a fifth object of the present invention to provide a material for capturing microbes or the like, a device for capturing microbes or the like, a method of capturing microbes or the like, and a method of producing the material for capturing microbes or the like, suitable for handling microbes or the like such as bacteria without requiring transport of samples, because a simple apparatus having a small-scale structure can be used, thereby enabling to perform treatment at a site where a sample to be tested is present.

It is a sixth object of the present invention to provide a method of storing microbes or the like whereby microbes which are the target in a specimen, can be stored with a high survival rate.

[Non-Patent Document 1] "Interface and Microbes", written by Hisao Morisaki and Reiko Hattori, published by Academy Publishing Center, 1986, pages 14, and 92-103

Means for Solving the Problems

To solve the above-described technical problems, a first aspect of the invention relates to a material for capturing microbes or the like, which comprises irregular-shaped powdery grains made of a pulverizable adsorbent resin and distributed in a predetermined grain size range, and which can adsorb or bond to a target contained in a liquid.

Here, "pulverizable resin" means an insoluble resin being a solid at normal temperature, and firstly, is a natural resin, a synthetic fiber, or a predetermined synthetic resin, with small elasticity and somewhat large orientation and crystallinity. Secondly, when the elasticity is larger than the first case and is not suitable for pulverization, the pulverizable resin is a resin in a glass state at a temperature equal to or lower than the glass transition temperature, or a resin in a state at a temperature equal to or lower than the glass transition temperature and equal to or lower than a low-temperature brittle point. Here, as the natural resin in the first case, there is chips containing natural cellulose. As the synthetic fiber in the first case, there can be mentioned nylon, vinylon, acrylic fiber, and rayon. As the predetermined synthetic resin in the first case, there is a thermosetting resin in which a prepolymer having a small degree of polymerization (a curing agent may be added thereto) is heated and a three-dimensional crosslink is formed between molecules. The thermosetting resin includes a formaldehyde resin and a crosslinking resin. The formaldehyde resin performs crosslinking and curing by a condensation reaction with formaldehyde, and includes a phenol resin and an amino resin. The crosslinking resin performs crosslinking by using a reaction other than condensation with formaldehyde, and includes unsaturated polyester resin, diallyl phthalate resin, alkyd resin, epoxy resin, polyurethane resin, and silicone resin. As the resin in the second case, there can be mentioned a thermoplastic resin formed of, for example, natural rubber, synthetic rubber such as polyisoprene or butadiene, or a solid-state chain polymer, in which plasticity is generated by heating. As the thermoplastic resin, there can be mentioned, for example, vinyl chloride resin, polyethylene, and polypropylene.

The "pulverizable adsorbent resin" means an insoluble resin of the pulverizable resins, that has an adsorptive property or bondability with respect to a target described later, and includes a pulverizable ion exchange resin and other resins. As the pulverizable ion exchange resin, there are three types of ion exchange resins, that is; a pulverizable cation exchange resin, a pulverizable anion exchange resin, and a pulverizable amphoteric ion-exchange resin, provided with an ion-exhangeable acidic group and basic group, and using the pulverizable resin described above as a matrix. As a matrix resin, it is more preferable that the resin is porous.

The pulverizable cation exchange resin is a polyacid in which an acidic group such as an acidic hydroxyl group, a carboxyl group, or a sulfonic group is bonded to a synthetic resin (R) in which polystyrene crosslinked with, for example, divinylbenzene is used as a matrix, wherein a hydronium ion $H_3O+$ is generated, which is exchanged with a base in water, or a cation of a neutral salt.

As a pulverizable cation exchange resin material, for example, weakly acidic MR cation exchange resin (Model No. C76AG by Organo Corporation) having an acrylic matrix structure, and strongly acidic gel-type cation exchange resin (Model No. IR120BNA by Organo Corporation) having a styrene matrix structure can be mentioned as commercially available ones, which are, respectively, in a true spherical shape having a grain size of about 0.5 mm.

The pulverizable anion exchange resin is a polymer base in which a basic group such as an amino group, an imino group, or an ammonium salt is bonded to a synthetic resin (R) in which polystyrene crosslinked with, for example, divinylbenzene is used as a matrix. As an ion exchange resin material of pulverizable anions, for example, weakly basic MR anion exchange resin (Model No. IRA96SB by Organo Corporation), strongly basic gel-type anion exchange resin (Model No. IRA410JCL by Organo Corporation), and very strongly basic gel-type anion exchange resin (Model No. IRA400JCL by Organo Corporation) can be mentioned as commercially available ones, which are, respectively, in a true spherical shape having a grain size of about 0.5 mm, and a matrix structure thereof is a styrene matrix structure. The amphoteric ion-exchange resin includes both an acidic group and a basic group as an exchange group. Generally, the ion exchange resin is recyclable and can be used repeatedly. The anion exchange resin also includes available products such as Mitsubishi Chemical, Diaion SA series, PA series, HPA series, and WA series.

The "other" pulverizable adsorbent resins described above include; a pulverizable chelate resin, a pulverizable adsorbent material, and a pulverizable ligand binding resin in which the pulverizable resin has a functional group, and a ligand having bondability to a receptor held by a target such as a microbe, a virus, or a biopolymer is bonded to the functional group as the other substances. Here, the ligand corresponds to biological materials of; genetic materials of nucleic acid, proteins, saccharides, peptide and the like having bondability to genetic material of nucleic acid and the like, proteins, saccharides, peptides, and the like, as the aforementioned receptor.

The "pulverizable chelate resin" is a pulverizable resin of resins that strongly select and adsorb specific ions by chelate bond, and combinations of (N, O), (N, S), and (O, O) can be used as a ligand involved with the chelate bond. There can be mentioned ethylenediaminetetraacetic acid (EDTA) or the like as the pulverizable chelate resin. As a chelate resin material of pulverizable cations, there can be mentioned, for example, chelate-resin MR cation exchange resin (Model No. IRC748 by Organo Corporation) as the commercially available one, in which the matrix structure thereof is a styrene matrix structure and is in a true spherical shape having a grain size of about 0.5 mm.

The pulverizable styrene resins or the above described various pulverizable porous resins in which microbes and the like are adsorbed by the pulverizable resin itself or by a pulverizable resin having a porous surface, without providing a functional group on the surface, correspond to the "pulverizable adsorbent material".

The "target", that is, an objective substance to be captured, is microbes or the like. The microbes or the like include: microbes of bacteria (Gram-negative bacteria (colon *bacillus*), Gram-positive bacteria (*staphylococcus*)), fungus (mold, yeast or the like), protozoa (for example, *cryptospo*-

*ridium* bacteria or the like), cells, or biomedical tissue; viruses; and biopolymers such as nucleic acid, protein, amino acid, fat, or saccharides, and include ones in which a surface thereof can be charged to positive or negative in a solution. Bacteria include bacteria dissolved in water, such as colon *bacillus* such as O157, *Legionella* bacteria, *salmonella*, and *dysentery bacillus*. The cells include for example, red blood cells, white blood cells, and blood platelets, and the biomedical tissue includes for example, nervous tissue and muscular tissue. The sizes thereof are in a range of from several nanometers to several microns.

Interaction between the irregular-shaped powdery grains and the target such as microbes, which causes "adsorption or bond", includes a case by chemical adsorption such as ionic bond, hydrophobic interaction, Coulomb's force, hydrogen bond, and coordinate bond, a case by physical adsorption, or a bond based on differential response acting between the receptor and ligand.

Here, the "predetermined grain size range" means a range of the size of irregular-shaped powdery grains determined: according to whether to treat a liquid containing the target such as microbes by causing the liquid to pass through a filter in which irregular-shaped powdery grains are held, or to process the liquid by suspending the irregular-shaped powdery grains in the liquid; according to a pore diameter of the filter in the case of using the filter; according to which amount of liquid is to be treated and for how long; according to what extent the target such as microbes is to be concentrated; according to the kind of the target; or according to which type of instrument is to be used for the treatment. The "grain size" indicates the size of powdery grains, and for example, can be an average diameter obtained from a mean value of lengths in two or more directions, or the Stokes' diameter.

The predetermined grain size range is such that an average grain size is from several nanometers to 500 microns, for example, as shown in a second aspect of the invention.

Because the powdery grains are distributed, the powdery grains are present multitudinously or in a predetermined amount described above so as to spread over the range. An example thereof is shown in FIG. 2.

The "irregular-shaped" shape is a three-dimensional shape in which a broken area or a broken surface that has been broken down and cut due to an impact force is formed. The irregular-shaped shape includes a case where a damaged surface or a damaged area that has been damaged upon reception of the impact force is formed, other than the broken area or the broken surface, and these include a flat surface or a curved surface of various shapes, or an irregular structure such as irregularities or striations. Therefore, for example, as shown in FIG. 10 (*b*), the irregular-shaped shape can include various complicated, and collapsed or deformed polyhedral shapes that cannot be specified. In correlations of respective powdery grains having the irregular-shaped shape, the shapes are uneven or nonuniform, and these do not have any congruence relation or similarity relation. The size of the three-dimensional shape is included in the predetermined range, as described above.

A second aspect of the invention relates to a material for capturing microbes or the like, wherein the predetermined grain size range is such that an average grain size is from 1 nm to 500 μm.

When the microbes are to be captured, the material for capturing microbes or the like has an average grain size in a range equal to or larger than 1 μm, and preferably, from 25 μm to 250 μm. When viruses or biopolymers are to be captured, the material for capturing microbes or the like has an average grain size in a range of equal to or larger than several nanometers. The reason why 25 μm is specified here is that a commercially available filter that can allow passage of powdery grains having a grain size smaller than this can be used. Moreover, in the case of a grain size larger than 250 μm, if a suspension having a grain size larger than 250 μm is handled by a pipette tip having a volume of 1 mL, clogging may occur at the neck at the end thereof, thereby causing a problem in the treatment. More preferably, the average grain size is in a range of from about 30 μm to about 100 μm, in which microbes, particularly, bacteria of about 1 μm are adsorbed or bonded in a large quantity to a surface of the material for capturing microbes or the like, so that the powdery grains cohere via the microbes and precipitate, whereas when the microbes are not adsorbed or bonded, the powdery grains become a suspended state.

It is desirable that the irregular-shaped powdery grains are washed or sterilized. Here, "washing" is performed in such a manner that the irregular-shaped powdery grains are suspended in a cleaning solution or stirred therein. As the "cleaning solution", sterilized distilled water or ethanol is used.

The ion exchange resin is, for example, a strongly basic gel-type, a very strongly basic gel-type, or a weakly acidic MR ion exchange resin.

When the microbes or the like are normal bacteria such as colon *bacillus* or *tubercule bacillus*, particularly, the microbes have a high adsorptive property or bondability with respect to the strongly basic gel-type and very strongly basic gel-type pulverizable resin. The *Legionella* bacteria have a high adsorptive property or bondability with respect to the weakly acidic MR pulverizable resin.

The strongly basic gel-type and very strongly basic gel-type irregular-shaped powdery grains are styrene anions, and the weakly acidic MR irregular-shaped powdery grains are acrylic cations.

A third aspect of the invention relates to a material for capturing microbes or the like wherein the pulverizable adsorbent resin includes a pulverizable ion exchange resin, a pulverizable chelate resin, or a pulverizable absorbent.

A fourth aspect of the invention relates to a method of producing a material for capturing microbes or the like including a step of pulverizing an adsorbent resin material made of a pulverizable adsorbent resin to form irregular-shaped powdery grains distributed in a predetermined grain size range.

Here, the "adsorbent resin material" is a material formed of the adsorbent resin, and is adsorbent resin grains including molded grains having a uniform shape such as a true spherical shape and a uniform grain size or grain diameter. The adsorbent resin grains are, for example, commercially available grains having a true spherical shape with a grain diameter of about 0.5 mm. The "predetermined grain size range" is as described above.

In the step of pulverizing the adsorbent resin material to form irregular-shaped powdery grains, pulverizing efficiency is increased by removing moisture held in gaps present in the pulverizable adsorbent resin material. Therefore, it is desired that the pulverizing step includes a drying step for drying the adsorbent resin material.

A fifth aspect of the invention relates to a method of producing a material for capturing microbes or the like further including a step of classifying the generated irregular-shaped powdery grains into grain size ranges in a plurality of predetermined bands.

The "grain size ranges in a plurality of predetermined bands" refer to a case where the grain size of the irregular-shaped powdery grains is divided into a plurality of bands of grain size, for example; a range of from 25 μm to 90 μm, a range of from 90 µm to 250 µm, a range of from 25 µm to 46 µm, a range of from 46 µm to 90 µm, and a range of from 90 µm to 180 µm. The grain size range of the powdery grains to be used is determined for example; by a range determined by experiments, by target types, by a treatment object, by a pore diameter of a filter for classifying easily available powdery grains, or by a pore diameter of a filter to be used for separating the irregular-shaped powdery grains from a liquid.

When the grain size is in a range less than about 90 µm, the irregular-shaped powdery grains have a small settling velocity and are easily suspended in a liquid. Therefore, by suspending the irregular-shaped powdery grains in a liquid, targets such as microbes can be brought into contact with the powdery grains. In this case, this is performed by filtering a suspension in which the powdery grains are suspended, by a filter in a contact step. Accordingly, adsorption time can be reduced. Moreover, the irregular-shaped powdery grains in this grain size range are held in a flow channel, and a small amount (for example, less than 50 mL) of liquid is introduced into the flow channel to bring the targets into contact with the powdery grains. In this case, however, it is desired to close the flow channel to circulate the liquid.

When a small amount of sample solution is handled, the amount of the irregular-shaped powdery grains to be used is determined, taking into consideration; that a dissociation solution is required at the time of collecting the targets such as microbes contained in the sample solution, that the amount of dissociation solution is proportional to a surface area of the irregular-shaped powdery grains to be used, and that the targets such as the microbes are concentrated by the treatment. For example, when the amount of the sample solution is 10 mL, the amount of dissociation solution needs to be 200 µL or less in order to set a concentration factor to 50 times. Then, it is appropriate that the "predetermined amount" of the irregular-shaped powdery grains to be suspended and used in a fifteenth aspect of the invention described later is in a range of from 20 mg to 40 mg.

Furthermore, when the grain size is in the range of about 90 µm or larger, it is desired that the irregular-shaped powdery grains are not suspended but held in the flow channel, and the targets are brought into contact with the irregular-shaped powdery grains by introducing the liquid into the flow channel. In this case, concentration treatment can be performed with respect to a large amount (for example, from about 50 mL up to about 10 L) of liquid.

When the grain size is in the range of 90 µm or larger, it is appropriate that ion exchange powdery grains are held in the flow channel and brought into contact with the targets by introducing the liquid into the flow channel. For example, when a filter having a diameter of 12 mm is used in the flow channel, it is appropriate that the "predetermined amount" of the irregular-shaped powdery grains in the fifteenth aspect of the invention described later is about 200 mg, in order to treat a liquid of 10 L to obtain a dissociation solution of 500 µL.

It is desired that the method of producing the material for capturing microbes or the like includes a step of washing or sterilizing the irregular-shaped powdery grains.

It is also desired that the washing or sterilizing is performed for each kind.

A sixth aspect of the invention relates to a device for capturing microbes or the like including; irregular-shaped powdery grains made of a pulverizable adsorbent resin and distributed in a predetermined grain size range, an irregular-shaped powdery-grains holding section that allows passage of a liquid and holds the irregular-shaped powdery grains so as to be able to come in contact with the passing liquid, and a container that receives the liquid having passed through the irregular-shaped powdery-grains holding section.

The "irregular-shaped powdery grains" are the ones described in any one of the first to third aspects of the invention. Passage of the liquid is not necessarily limited to a case where the liquid moves in a flow channel having a port, and includes, for example, a case where the liquid moves in a liquid channel such that the liquid drops downward in the air from above, without using the flow channel.

The "irregular-shaped powdery-grains holding section" can be, for example, one in which the irregular-shaped powdery grains are held by being placed on one filter having a pore diameter smaller than the predetermined grain size range, or an irregular-shaped powdery-grains enclosing column in which the powdery grains are placed between two filters and enclosed therein. In the case of using one filter, for example, when the powdery grains are placed on one filter in a flow channel extending vertically, and a liquid is caused to flow in one direction, downward from above, the powdery grains are formed in layers.

For example, when the irregular-shaped powdery-grains holding section is provided in a flow channel having two ports for respectively performing suction and discharge, the irregular-shaped powdery-grains holding section is provided with two filters so as to partition the flow channel interior, and the irregular-shaped powdery grains are held by being placed between the filters. A partial tube of the flow channel can be provided detachably from the flow channel, and provided so that openings at the opposite ends of the tube are covered by filters. When the powdery grains are held by being placed between the two filters, there is a case where the powdery grains are held in layers by decreasing the distance between the filters to decrease the freedom of the powdery grains, and a case where the powdery grains are held in layers by increasing the distance between the filters to increase the freedom of the powdery grains. The former case is suitable for a case where the concentration of the targets is small so that clogging does not occur in the irregular-shaped powdery-grains holding section. The latter case is suitable for a case where concentration of the targets is large so as to cause clogging in the irregular-shaped powdery-grains holding section.

Moreover, when the irregular-shaped powdery-grains holding section is a tip-like container used in a dispensing burette in which a flow channel has one port for performing suction and discharge, the irregular-shaped powdery-grains holding section may hold the irregular-shaped powdery grains in a space between filters, in such a manner that the tip-like container is formed of a small diameter portion and a large diameter portion, a stepped portion is provided in a transition part between the small diameter portion and the large diameter portion, a filter is provided so as to be supported by the stepped portion and vertically partition the tip-like container along an axial direction, and the irregular-shaped powdery grains are provided on top of the filter, or another filter is provided above the filter with a space therebetween to hold the irregular-shaped powdery grains in the space. When the tip-like container is used, because suction and discharge can be repeated, efficiency of adsorption or bonding of the irregular-shaped powdery grains to the targets is high.

A seventh aspect of the invention relates to a device for capturing microbes or the like further including a flow channel in which one or a plurality of ports for performing liquid suction or discharge are provided and a liquid can move therein, and a pressure adjusting mechanism for adjusting pressure in the flow channel. The irregular-shaped powdery-grains holding section occupies a certain area of the flow channel, and the container is provided outside the flow channel so that the one or the plurality of ports can be inserted therein.

For example, the flow channel is a tip-like container having one port and one fitting opening, and the pressure adjusting mechanism includes a suction/discharge mechanism that performs suction and discharge of a liquid with respect to the tip-like container via the port, and a nozzle communicating with the suction/discharge mechanism. The tip-like container is detachably mounted on the nozzle at the fitting opening. The suction/discharge mechanism is provided with, for example, a cylinder and a piston inserted into and fitted to the cylinder so as to slide therein, in which the piston is driven by, for example, a motor and a ball screw mechanism. The port preferably has a shifting means whereby it can be shifted relative to the container.

Thus, the tip-like container is used to introduce the liquid through the port into the tip-like container, so as to come in contact with the irregular-shaped powdery grains, and to discharge the liquid through the same port. Therefore, because the liquid can be made to flow in both directions through the same port, even a minute amount of liquid can come in contact with the irregular-shaped powdery grains efficiently and reliably. Moreover, by moving the tip-like container, contact between various liquids and the irregular-shaped powdery grains is realized, and hence, the device for capturing microbes or the like is suitable for automating the entire treatment consistently.

Moreover, it is desired to control the size of pressure in the flow channel due to the pressure adjusting mechanism and the time thereof by means of a control section based on; the structure of the flow channel, the kind of the irregular-shaped powdery grains held by the irregular-shaped powdery-grains holding section, the grain size or amount, the amount or kind of the liquid, the kind, concentration factor, or concentration of the target, the treatment object, and the treatment time.

"The container is provided outside the flow channel" means that the container and the flow channel are not connected to each other, or are not directly communicated with each other.

An eighth aspect of the invention relates to a device for capturing microbes or the like wherein the container includes a stirring container provided so as to be rotatable about an axis of rotation penetrating the container, and provided with a stirring wall protruding from an inner wall of the container toward the axis of rotation.

The container preferably has a shape close to a rotor, in view of a rotation operation. It is preferable to form the inner wall of the container in rotational symmetry. It is also preferable that the stirring wall has a surface extending in a range not exceeding the axis of rotation, and having a certain height in a direction along the axis of rotation.

A ninth aspect of the invention relates to a device for capturing microbes or the like wherein the plurality of ports of the flow channel are a suction port for sucking a liquid and a discharge port for discharging a liquid, the pressure adjusting mechanism is for sucking a liquid from the suction port and causing the liquid to flow out from the discharge port, and the irregular-shaped powdery-grains holding section is provided between the suction port and the discharge port of the flow channel.

Here the suction port and the discharge port are preferably used by both being inserted into the container.

It is desired that the container has the axis of rotation penetrating the container vertically so as to be able to rotate the container, a protrusion protruding toward the inside of the container is provided, and the container is provided rotatably about the axis of rotation. Accordingly, by rotating a suspension stored in the container, the stored suspension can be stirred. For this purpose, a rotation mechanism having a motor or the like that rotates the container about the axis of rotation is provided. Accordingly, treatment can be performed while maintaining the suspended state, without causing a substance suspended in the suspension to subside, and hence treatment can be performed efficiently and reliably with respect to the suspended substance.

Moreover, the device for capturing microbes or the like includes a reservoir communicated with the suction port and the discharge port via the flow channel, for accumulating the sucked liquid, and the pressure adjusting mechanism can be one that adjusts the pressure in the flow channel by adjusting the pressure in the reservoir. In this case, the pressure adjusting mechanism includes an air passage provided in the reservoir, a pump that performs suction and discharge of gas in the reservoir via the air passage, and a valve, or includes a cylinder, a piston inserted into and fitted to the cylinder so as to slide therein, and a valve.

A tenth aspect of the invention relates to a device for capturing microbes or the like wherein the irregular-shaped powdery-grains holding section has at least one filter having a pore diameter smaller than the predetermined grain size range of the irregular-shaped powdery grains.

As the grain size of the irregular-shaped powdery grains becomes smaller, the pore diameter of the filter becomes smaller, and when a certain amount is to be treated within a certain period of time, the pressure required for passage of the liquid increases.

Therefore, a control section having a built-in computer that performs information processing is provided in the device for capturing microbes or the like, to determine; an amount of liquid to be introduced, the pressure of the pressure adjusting mechanism, or the set time thereof, based on a parameter selected from; the amount and range of grain size of the ion exchange powdery grains, the pore diameter of the filter to be used, the thickness of the filter, the diameter of the powdery grains, or a concentration factor (dilution ratio) or concentration to be obtained. The liquid contains, for example, a dissociation solution for dissociating the targets such as microbes adsorbed and bonded, or captured from the ion exchange powdery grains, such as a TRIS buffer. The final concentration of the targets such as microbes is determined based on the amount of dissociation solution.

When one filter is used in the irregular-shaped powdery-grains holding section, the filter is provided so as to partition the liquid passage direction or the flow channel. The liquid passage direction or the direction of the flow channel is downward from above, and the irregular-shaped powdery grains are placed on the filter.

When two filters are used in the irregular-shaped powdery-grains holding section, the liquid passage direction or the direction of the flow channel is not particularly limited, and the irregular-shaped powdery grains are provided so as to be placed between the two filters.

An eleventh aspect of the invention relates to a device for capturing microbes or the like wherein the irregular-shaped powdery-grains holding section is provided detachably with respect to the flow channel.

The irregular-shaped powdery-grains holding section has an irregular-shaped powdery-grains enclosing tube that encloses the irregular-shaped powdery grains therein so as to be able to come in contact with the introduced liquid.

It is desired that the device for capturing microbes or the like has a removal mechanism that detaches the irregular-shaped powdery-grains holding section from the flow channel.

When the flow channel is a tip-like container, the removal mechanism is a tip removal mechanism that detaches the tip-like container from the nozzle.

A twelfth aspect of the invention relates to a device for capturing microbes or the like wherein the flow channel is formed of an extendable elastic body, and has a peristaltic pump as a pressure adjusting mechanism.

A thirteenth aspect of the invention relates to a method of capturing microbes or the like comprising: a contact step in which liquid is brought into contact with a predetermined amount of irregular-shaped powdery grains, which are made of a pulverizable adsorbent resin and distributed in a predetermined grain size range; and a separation step in which the irregular-shaped powdery grains are separated from the liquid, and targets contained in the liquid are captured by adsorbing or bonding the targets to the irregular-shaped powdery grains.

The "predetermined amount" is determined, as explained in the sixth aspect of the invention, based for example, on the grain size range of the irregular-shaped powdery grains to be used, the amount of liquid to be treated, the desired concentration factor, and the like.

A fourteenth aspect of the invention relates to a method of capturing microbes or the like wherein the contact step includes a suction step for sucking a liquid from a container provided outside, into a flow channel by adjusting a pressure in the flow channel, and the separation step includes a discharge step for discharging the liquid brought into contact with the irregular-shaped powdery grains from the flow channel, with the irregular-shaped powdery grains being held in the flow channel, by adjusting the pressure in the flow channel.

When the flow channel is a tip-like container having one port, in the contact step, the liquid is sucked through the port and brought into contact with the irregular-shaped powdery grains, and in the separation step, the liquid is discharged from the port, with the irregular-shaped powdery grains being held in the tip-like container. On the other hand, a case where the flow channel is a tip-like container having two ports is shown in a seventeenth aspect of the invention below.

A fifteenth aspect of the invention relates to a method of capturing microbes or the like wherein in the contact step, a suction port for sucking the liquid in the flow channel and a discharge port for discharging the liquid are inserted into the same container, and the liquid is brought into contact with the irregular-shaped powdery grains by causing the liquid to flow in one direction from the suction port toward the discharge port through the flow channel. In the separation step, the liquid is discharged from the discharge port to the container, with the irregular-shaped powdery grains being held in the flow channel.

A sixteenth aspect of the invention relates to a method of capturing microbes or the like further including a collection step for collecting the targets adsorbed or bonded to the irregular-shaped powdery grains.

It is desired that the collection step has a separation step for separating the targets such as microbes captured by being adsorbed or bonded to the irregular-shaped powdery grains from the irregular-shaped powdery grains. Generally, a second amount of liquid due to the dissociation solution used in the collection step is smaller than a first amount of liquid introduced into the flow channel and containing the targets such as microbes. In the dissociation step, it is desired that dissociation is performed by stirring or shaking the irregular-shaped powdery grains in the dissociation solution.

A seventeenth aspect of the invention relates to a method of capturing microbes or the like wherein in the collection step, the irregular-shaped powdery grains are collected by detaching the irregular-shaped powdery-grains holding section that holds the irregular-shaped powdery grains to which the targets are adsorbed or bonded, from the flow channel.

An eighteenth aspect of the invention relates to a method of capturing microbes or the like wherein when the contact step is performed, the liquid stored in the container is being stirred.

A nineteenth aspect of the invention relates to a method of storing microbes or the like storing targets, including a suspension step for suspending a predetermined amount of irregular-shaped powdery grains made of a pulverizable adsorbent resin and distributed in a predetermined grain size range, in a liquid containing targets.

When the targets are predetermined microbes such as bacteria, it is desired to have a holding step for holding the liquid in which the powdery grains are suspended at a predetermined temperature, for example, at a low temperature of 4° C. Moreover, the liquid and the powdery grains are held and stored in a predetermined container.

Effects of the Invention

According to the first, sixth, or thirteenth aspects of the invention, the powdery grains having an irregular-shaped shape with the grain size being distributed in a predetermined range has a considerably large surface area, as compared with a normal carrier having a uniform shape such as sphere and a grain diameter of a size corresponding to the grain size, or the pulverizable adsorbent resin grains. Therefore, the capturing efficiency for adsorbing the targets of microbes such as bacteria, viruses, cells, biomedical tissues, nucleic acid, protein, fat, or saccharides or biopolymers (microbes or the like) in the liquid can be further increased. Moreover, adsorption or bonding points coming in contact with the targets increase due to irregular unevenness on the surface of the irregular-shaped powdery grains, thereby enabling to further increase the adsorptive power or bonding power.

Moreover, irregular-shaped powdery grains in which the grain size of the irregular-shaped powdery grains is not uniform or constant, and is distributed in a predetermined range are used. Therefore, the irregular-shaped powdery grains can be filled more densely as compared with a case where grains having a uniform shape and a certain grain size (for example, the average grain size in the above-described range) are filled in the same amount and in the same area. Accordingly, the gap between grains is further narrowed down and the encounter rate with targets such as microbes suspended in the liquid which passes through the gap, can be further increased. Consequently, the distance of the passage of the liquid between the grains can be increased, to further increase the opportunity of reaction. Therefore, targets such as microbes can be captured more reliably and more efficiently.

According to the present invention, a large-scale apparatus is not required, and a concentration operation can be performed, not in a laboratory, but at a site where a sample to be tested is present. Therefore, the sample as a test object need not be transported. Moreover, a large volume (for example, 500 mL or more) of concentration operation can be performed easily, which is difficult in a centrifugal operation or filter operation. Therefore, labor can be reduced. Furthermore, the present invention can be directly connected to a detection method which requires concentration at high concentrations such as immunochromatography (antigen-antibody reaction is caused on test paper, to obtain antigen concentration by color development of the test paper corresponding to a reaction amount), which is difficult in the centrifugal operation or filter operation. Furthermore a simple operation is possible by a person other than a tester who has received training as a researcher or the like.

According to the second aspect of the invention, the material for capturing microbes or the like is suitable for adsorbing or bonding targets such as microbes having a size of from 1 nanometer to several microns, and commercially available various classification tools can be used. The material for capturing microbes or the like is also suitable for treatment using a dispenser tip.

When the powdery grains are used enclosed in an irregular-shaped powdery-grains enclosing column 32, then instead of using a filter that can directly collect targets such as microbes having a size of from 1 nanometer to several microns, a filter having a larger pore diameter capable of enclosing grains that can bond or capture the targets is used. Therefore a more simple peristaltic pump using relatively low pressure can be used to perform treatment without causing clogging. Consequently, for example, a specimen of up to 10 liters can be concentrated to 1 mL (at a concentration factor of 10000 times) or 0.5 mL (at a concentration factor of 50000 times).

Thus, by improving the concentration factor, sensitivity in a detection system can be improved. Then, for example, a detection method using the immunochromatography method can be applied, thereby enabling to perform quick detection at the site. According to the immunochromatography method, differential detection with a specific serotype of *Legionella* bacteria can be performed quickly at the site. Moreover, according to the culture, all of the *Legionella* groups can be detected. Furthermore, according to the nucleic acid amplification, it is possible to select and detect a *Legionella* group, a species thereof, and a serotype thereof.

According to the third aspect of the invention, because the material for capturing microbes or the like can be pulverized at normal temperature, the material for capturing microbes or the like can be produced easily, with less labor, and at low cost.

According to the fourth aspect of the invention, the irregular-shaped powdery grains distributed in the predetermined grain size range can be generated easily and at low cost by pulverizing pulverizable adsorbent resin grains having a uniform shape and size beforehand. Moreover, by pulverizing the pulverizable resin grains, a large number of gaps present inside and on the surface of the pulverizable adsorbent resin grains can be exposed on the surface of a broken surface or a broken area. Therefore, unevenness or the like is formed to further increase the surface area, thereby enabling to obtain a strong adsorptive power or bonding power with the targets such as microbes.

According to the fifth aspect of the invention, by classifying the irregular-shaped powdery grains into grain size ranges in a plurality of bands, irregular-shaped powdery grains in a range matched with the treatment apparatus or with treatment conditions such as the amount of liquid can be used, and hence optimum treatment can be performed.

Moreover, by washing or sterilizing the irregular-shaped powdery grains, highly reliable treatment without contamination can be performed.

According to the seventh or fourteenth aspects of the invention, the flow channel is provided, a liquid containing the targets such as microbes is sucked from a container provided outside of the flow channel to come in contact with the irregular-shaped powdery grains by adjusting the pressure in the flow channel, and the liquid is discharged from the flow channel into the container in a state with the irregular-shaped powdery grains being held by the liquid in the flow channel, thereby enabling to perform separation, extraction, or collection of the targets easily by just adjusting of the pressure. Moreover, by controlling the size of the pressure and the time, treatment matched with: the grain size, the kind, and the amount of the irregular-shaped powdery grains; the amount and kind of liquid to be treated; the kind, concentration factor, and concentration of the targets; and the treatment object can be performed.

Particularly, according to the fourteenth aspect of the invention, treatment of a large amount of liquid can be performed reliably by causing the liquid to flow continuously.

According to the eighth or eighteenth aspects of the invention, when the liquid in the container is sucked and discharged, the liquid in the container is stirred. Therefore, precipitation of solids such as microbes or biopolymers in the liquid is prevented, and suction and discharge can be performed in a suspended state, thereby enabling to perform highly reliable treatment. Moreover stirring can be easily performed by just rotating the stirring container.

According to the ninth or fifteenth aspects of the invention, the liquid is caused to flow in just one direction in the flow channel. Therefore, irregular-shaped powdery grains and targets such as microbes can be brought into contact with each other reliably with a simple operation over time, by circulating a large or small amount of liquid.

According to the tenth aspect of the invention, by using at least one filter having a pore diameter smaller than the predetermined grain size range for the irregular-shaped powdery-grains holding section, and causing the liquid to pass through the filter, the irregular-shaped powdery grains can be reliably held in the flow channel while being in contact with the liquid.

According to the eleventh or seventeenth aspects of the invention, the targets can be collected reliably and efficiently, by detaching the irregular-shaped powdery-grains holding section that holds the irregular-shaped powdery grains to which the targets such as microbes are adsorbed or bonded, from the flow channel. Moreover, by providing a detachable mechanism, a series of treatments including various steps can be automatically performed consistently.

According to the twelfth aspect of the invention, the flow channel can be freely set by forming the flow channel by an elastic body, and a closed channel can be formed, thereby enabling to circulate the liquid. Moreover, because the liquid can be caused to flow by providing a peristaltic pump, direct contact between the liquid in the flow channel and the pressure adjusting mechanism can be prevented, thereby enabling to reliably prevent cross-contamination.

According to the sixteenth aspect of the invention, a useful compound contained in the liquid can be extracted reliably and easily by collecting the targets from the irregular-shaped powdery grains to which the targets are adsorbed or bonded.

According to the nineteenth aspect of the invention, by suspending the powdery grains in the liquid containing the targets of microbes such as bacteria, targets can be stored with a high survival rate. Therefore, sampled specimens can be carried from a site to a predetermined inspection institution to perform highly accurate inspection, without using a large-scale apparatus.

BRIEF DESCRIPTION OF THE DRAWINGS

FIG. 1 is a flow chart illustrating a method of producing a material for capturing microbes or the like according to a first embodiment of the present invention.

FIG. 2(1) is a graph showing a grain size distribution of the respective materials for capturing microbes or the like according to the first embodiment of the present invention.

FIG. 2(2) is a graph showing another grain size distribution of the respective materials for capturing microbes or the like according to the first embodiment of the present invention.

FIG. 2(3) is a graph showing yet another grain size distribution of the respective materials for capturing microbes or the like according to the first embodiment of the present invention.

FIG. 4(a) is a top plan view of a stirring container in the device for capturing microbes or the like according to the second embodiment of the present invention.

FIG. 4(b) is a perspective view of the stirring container of FIG. 4(a).

FIG. 4(c) is an exploded perspective view of the stirring container of FIGS. 4(a) and 4(b) and a rotation drive section in the device for capturing microbes or the like according to the second embodiment of the present invention.

FIG. 8 is a diagram showing the utility of a material for capturing microbes or the like using the device for capturing microbes or the like according to the second embodiment of the present invention.

FIG. 10 (a) is an electronic microscope image of a number of irregular-shaped powdery grains, according to the fifth embodiment of the present invention.

FIG. 10 (b) is an electronic microscope image of a number of colon bacillus adsorbed to one irregular-shaped powdery grain, according to the fifth embodiment of the present invention.

FIG. 10(c) is an electronic microscope image of the irregular-shaped powdery grain, according to the fifth embodiment of the present invention.

FIG. 12(a) is a table illustrating treatment results using the device for capturing microbes or the like or the method of capturing microbes or the like according to the third embodiment of the present invention.

FIG. 12(b) is a table illustrating rate of adsorption to powdery grains according to the third embodiment of the present invention.

FIG. 12(c) is a table illustrating other treatment results using the device for capturing microbes or the like or the method of capturing microbes or the like according to the third embodiment of the present invention.

FIG. 13(a) is a table illustrating yet other treatment results using the device for capturing microbes or the like or the method of capturing microbes or the like according to the third embodiment of the present invention.

FIG. 13(b) is a table illustrating adsorption rates using the device for capturing microbes or the like or the method of capturing microbes or the like according to the third embodiment of the present invention.

FIG. 14 is a table illustrating a treatment using the device for capturing microbes or the like or the method of capturing microbes or the like according to the third embodiment of the present invention.

Figure 1:
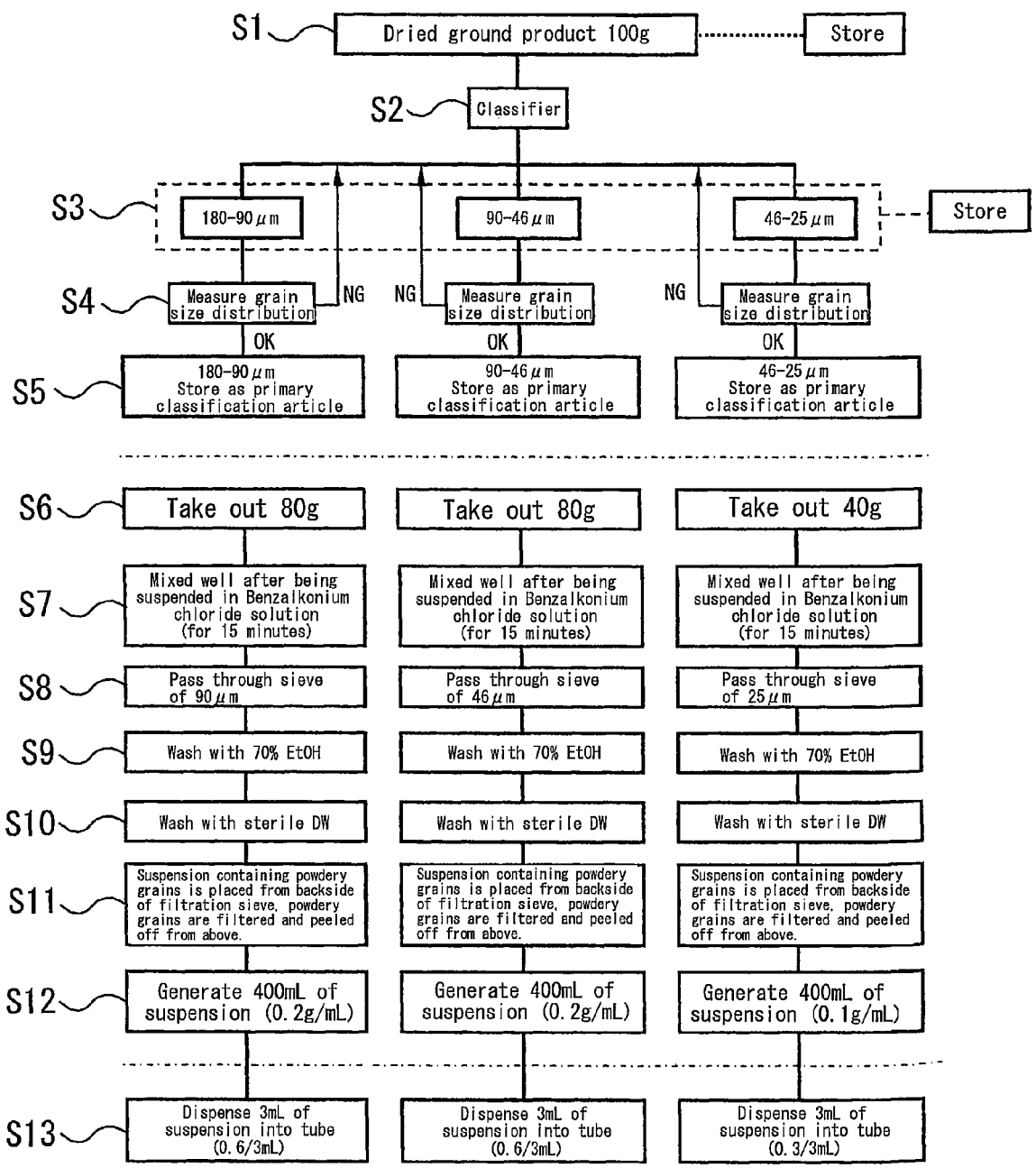

BRIEF DESCRIPTION OF THE REFERENCE SYMBOLS 10, 58, 68 Device for capturing microbes or the like
14, 60, 70 Microbes or the like capturing section
11 Irregular-shaped powdery grains (material for capturing microbes or the like)
16 Stirring container
23, 61 Suction port
24, 62 Suction flow channel
25 Discharge port
26 Discharge flow channel
32 Irregular-shaped powdery-grains enclosing column
34 Detaching machine

BEST MODE FOR CARRYING OUT THE INVENTION

FIG. 1 and FIG. 2 illustrate a method of producing a material for capturing microbes or the like according to a first embodiment of the present invention. The material for capturing microbes or the like according to the first embodiment is irregular-shaped powdery grains made of a pulverizable adsorbent resin, and is produced by pulverizing an ion exchange resin material formed of an ion exchange resin, which uses a pulverizable, insoluble, and porous synthetic resin as a matrix, into a predetermined grain size range.

As shown in the flow chart in FIG. 1, the manufacturing method according to the first embodiment roughly includes a pulverizing step for producing powdery grains with a targeted grain size of from 10 μm to 100 μm by using a pulverizer (corresponding to step S1), a classification step for screening the powdery grains to classify the powdery grains into three bands of grain size (grain diameter ranges), that is, 180 μm to 90 μm, 90 μm to 46 μm, and 46 μm to 25 μm (corresponding to steps S2 to S5), and a powdery grains treatment step for performing various treatments so that the classified powdery grains can be used as the material for capturing microbes or the like (corresponding to steps S6 to S13).

Step S1 corresponding to the pulverizing step is for pulverizing an unpulverized ion exchange resin material as the adsorbent resin in which, for example, three kinds of pulverizable resins are used as the matrix. As the ion exchange resin material, test number (1) is a wet item IRA400JCL (Organo Corporation), which is very strongly basic gel-type styrene anion exchange resin, test number (2) is a wet item IRA410JCL (Organo Corporation), which is a strongly basic gel-type styrene anion exchange resin, and test number (3) is a wet item IRC76AG (Organo Corporation), which is a weakly acidic MR acrylic cation exchange resin. True spherical ion exchange resin grains having a grain size of about 0.5 mm were used, respectively.

In the pulverizing step, a pulverizer (for example, a desktop impact type pulverizer (sample mill ASM)) is used to perform pulverization at a speed within a maximum rotation speed of 16000 min$^{-1}$ thereof. The purpose of this treatment is to form a large number of powdery grains in a range of 90 μm to 150 μm. The screen diameter is set to 0.5 mm or 0.3 mm.

FIG. 2 shows measurement results of distribution of grain size pulverized by the pulverizer for test numbers (1), (2), and (3). As a result, as an average grain size, 107 μm was obtained in test number (1), 108 μm was obtained in test number (2), and 111.9 μm was obtained in test number (3). The distribution of the grain size was measured by using a grain size distribution analyzer (for example, SALD-2000J by Shimadzu Corporation).

Steps S2 to S5 in FIG. 1 correspond to the classification step, where the irregular-shaped powdery grains obtained in step S1 are classified by a classifier by screening the grain diameter as the grain size into three bands of, for example, a range of 180 μm to 90 μm, a range of 90 μm to 46 μm, and a range of 46 μm to 25 μm.

In step S2, the irregular-shaped powdery grains are dried, and then 100 g of irregular-shaped powdery grains are placed into the classifier, for one kind of the ion exchange resins serving as the adsorbent resin.

The classifier includes: for example, four types of cylindrical bodies coaxially connectable to each other, having a diameter of 200 mm, and each provided with one stainless steel filter having different pore diameters from each other; a lid with fixing bracket connectably provided at an upper end of each cylindrical body and provided with a plurality of fixing brackets extending along the axial direction for fixing by screwing the cylindrical bodies connected to and overlapped on each other; a receptacle connectably provided at a lower end of each cylindrical body; and a shaker that shakes an assembly of the lid with fixing bracket, the four types of cylindrical bodies, and the receptacle connected to and overlapped on each other, and fixed by the fixing bracket.

The respective types of filters provided in the four types of cylindrical bodies are the stainless steel filters having pore diameters different from each other, and the pore diameters are, for example, 180 μm, 90 μm, 46 μm, and 25 μm. In the respective cylindrical bodies, the filter is provided so as to horizontally cross the axis of the respective cylindrical bodies and partition the cylindrical bodies vertically.

The classifier sets the assembly of the lid with fixing bracket, the cylindrical bodies respectively having a pore diameter of 180 μm, 90 μm, 46 μm, and 25 μm, and the receptacle connected in this order and overlapped on each other and fixed by the fixing bracket, in the shaker to shake these. Therefore, the irregular-shaped powdery grains placed into the classifier are stored in the cylindrical body having the filter with the pore diameter of 180 μm.

At this time, the screws of the fixing bracket are uniformly tightened, to securely fix the shaker and the respective cylindrical bodies, and the shaker is switched on to shake the cylindrical bodies for 30 minutes at a maximum speed.

After shaking the cylindrical bodies, the cylindrical bodies are removed in descending order. At this time, attention needs to be paid so that the powdery grains classified by the other filters are not mixed. The classification of the classified powdery grains is as described below. That is, 25 μm to 46 μm, 46 μm to 90 μm, and 90 μm to 180 μm.

In step S4, the grain size distribution is measured for the irregular-shaped powdery grains in the respective ranges screened in step S3 to confirm that the number of the grain size distributions outside of a targeted classification range is 20% or less. In step S5, a specified amount of the powdery grains is sampled and placed into a 250 ml sterile bottle in which 150 ml of sterilized Benzalkonium chloride solution (0.1%) is stored, and stored as a primary classification article. In step S3, the unclassified powdery grains are stored separately.

In step S6, of the classified irregular-shaped powdery grains serving as the material for capturing microbes or the like, 80 g is sampled in one treatment for the range of 46 μm to 90 μm and the range of 90 μm to 180 μm, as the predetermined grain size range, and 40 g of powdery grains is sampled for the range of 25 μm to 46 μm.

In step S7, the sampled irregular-shaped powdery grains are suspended in 150 μm of Benzalkonium chloride solution and stirred well for 15 minutes. As a result, bacteria attaching to the irregular-shaped powdery grains are peeled off, and a removal operation of unclassified powdery grains is performed.

In step S8, the suspension generated in step S7 is filtered by using a filtration sieve formed of three types of stainless steel filters having the targeted respective classification grain sizes, that is, a pore diameter of 90 μm, and 25 μm, and having a diameter of 200 mm. Filtration is performed so that the suspension is spread uniformly on the filter. The filtered liquid is removed.

In step S9, 500 ml of 70% ethanol is placed into a suspension bottle, and the remaining irregular-shaped powdery grains are re-suspended to be cleaned, and then the suspension is filtered by the filtration sieve formed of the stainless steel filter.

In step S10, 200 ml of sterile distilled water (DW) is placed into the suspension bottle instead of the ethanol, and the remaining irregular-shaped powdery grains are re-suspended to be further cleaned, the suspension is filtered by the filtration sieve formed of the stainless steel filters, and the liquid is well drained.

In step S11, the filtration sieve is inverted and placed on a funnel. A 500 ml bottle is attached to the under side of the funnel, and the irregular-shaped powdery grains are peeled off from the filtration sieve from the backside thereof.

In step S12, 400 ml of sterile distilled water is applied so as to wash by using an electric pipetter from the backside of the filtration sieve, and the irregular-shaped powdery grains held on the filtration sieve (stainless filter) are peeled off to generate 400 ml of suspension. Therefore, for the irregular-shaped powdery grains having a grain diameter of from 46 μm to 180 μm, the concentration thereof becomes 0.2 g/ml, and for the irregular-shaped powdery grains having a grain diameter of from 25 μm to 46 μm, the concentration thereof becomes 0.1 g/ml.

In step S13, 375 ml of the generated suspension is dispensed into 125 tubes in an amount of 3 ml, and is subjected to treatment with respect to various specimens.

Figure 3:
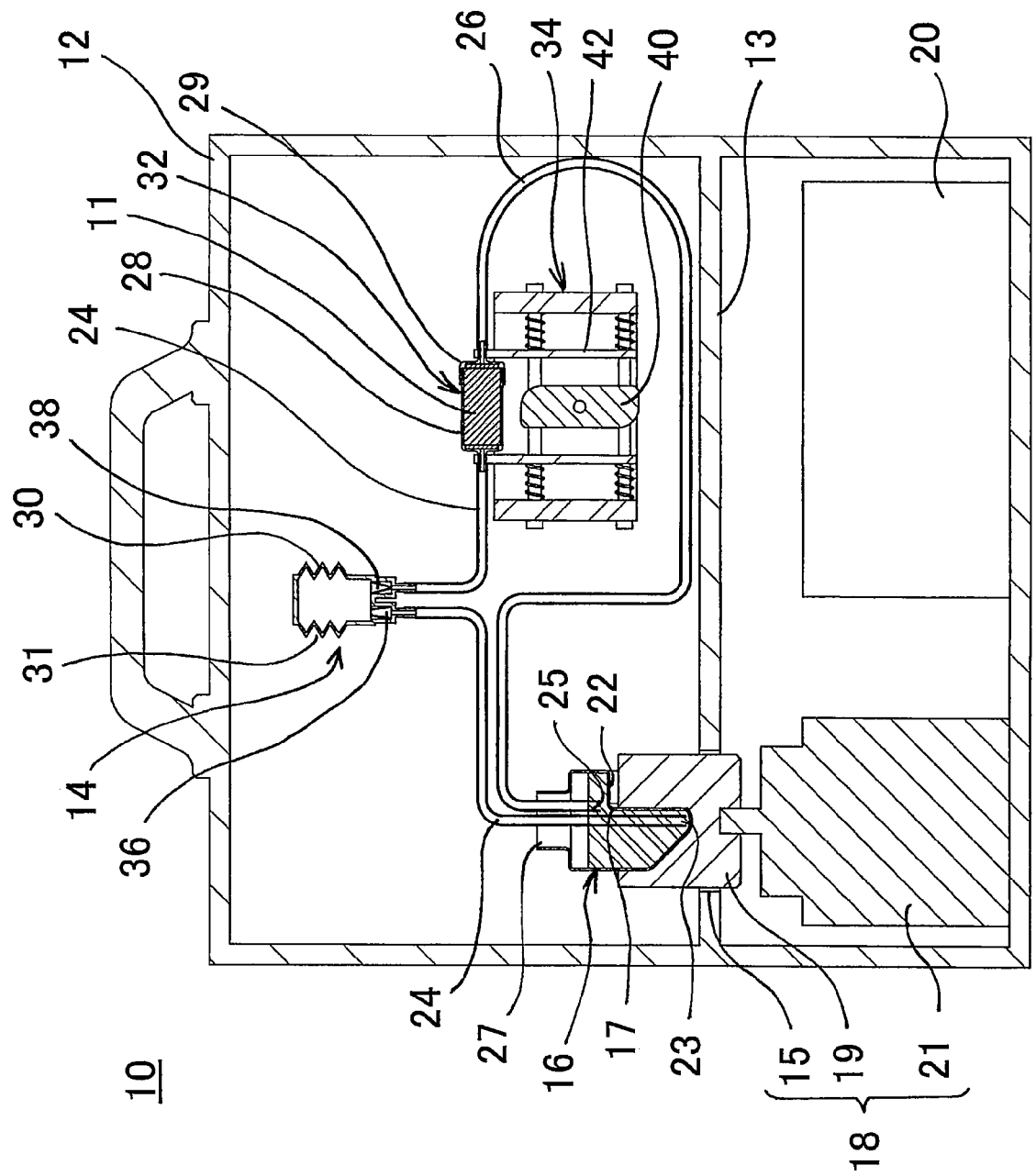
FIG. 3 is a sectional view of a device for capturing microbes or the like according to a second embodiment of the present invention.

A device for capturing microbes or the like 10 according to a second embodiment suitable for performing a treatment using irregular-shaped powdery grains 11 serving as the material for capturing microbes or the like will be explained with reference to FIG. 3.

The device for capturing microbes or the like 10 according to the second embodiment includes: a casing 12; a microbes or the like capturing section 14 housed above a partition plate 13 provided in the casing 12; a stirring container 16 having a stirring wall 17 protruding inward from an inner wall; a rotation drive section 18 provided to penetrate a hole 15 in the partition plate 13 to rotate the stirring container 16; and an electric circuit 20 housed below the partition plate 13 in which a control section that controls the microbes or the like capturing section 14 and the rotation drive section 18, and a power source are housed.

The microbes or the like capturing section 14 includes, as the flow channel, a suction flow channel 24 inserted into the stirring container 16 and having one suction port 23 through which suction of a liquid is performed, to thereby introduce the liquid into an irregular-shaped powdery-grains enclosing column 32, and a discharge flow channel 26 inserted into the stirring container 16 and having one discharge port 25 for discharging the liquid to discharge the liquid from the irregular-shaped powdery-grains enclosing column 32. The suction port 23 is provided at a position close to a bottom where the axis of rotation of the stirring container 16 passes so that substantially the whole amount of liquid stored in the stirring container 16 can be sucked. The discharge port 25 is preferably provided at a position away from the suction port 23 and near the axis of rotation, in an area where the liquid is stored in the stirring container 16.

The microbes or the like capturing section 14 includes a bellows pump 30 as a pressure adjusting section that adjusts the pressure in the flow channels 24 and 26. The bellows pump 30 has a bellows portion 31 that is compressed and restored by an upward and downward movement of an upward/downward movement mechanism (not shown) using a motor and a ball screw mechanism, and is provided in the suction flow channel 24. The bellows pump 30 has a one way valve 36 for causing the liquid to flow from the suction port 23 toward the bellows pump 30, and a one way valve 38 for causing the liquid to flow toward the discharge port 25.

In the microbes or the like capturing section 14, the irregular-shaped powdery-grains enclosing column 32 formed in the cylindrical container as the irregular-shaped powdery-grains holding section is provided detachably with respect to the flow channels 24 and 26. The irregular-shaped powdery-grains enclosing column 32 is connected in a certain area occupying a part of the flow channel, here, between the suction flow channel 24 and the discharge flow channel 26 so as to communicate therewith, and a predetermined amount of the irregular-shaped powdery grains 11 in the predetermined grain size range are enclosed therein as the material for capturing microbes or the like so as to be able to come in contact with the liquid sucked from the suction port 23.

In the irregular-shaped powdery-grains enclosing column 32, two filters 28 and 29 having a pore diameter smaller than the predetermined grain size range, are provided at opposite ends of the cylindrical container in a direction transverse to the axial direction of the irregular-shaped powdery-grains enclosing column 32 of the cylindrical container, that is, so as to partition the flow channel, and the irregular-shaped powdery grains in the predetermined grain size range are placed and enclosed between the filters 28 and 29, and held. The kind and amount of the irregular-shaped powdery grains inserted into the irregular-shaped powdery-grains enclosing column 32, the distance between the irregular-shaped powdery grains and the filters 28 and 29, and the volume of the irregular-shaped powdery-grains enclosing column 32 are preferably determined according to the kind, property, concentration, concentration factor, amount, or flow rate of the liquid.

Connection short tubes protrude outward, respectively, from the opposite ends of the irregular-shaped powdery-grains enclosing column 32 along the axial direction thereof, and are detachably connected and attached to the suction flow channel 24 and the discharge flow channel 26.

The device for capturing microbes or the like 10 further includes a column detaching machine 34 having two movable plates 42 driven by a cam 40 for attaching or detaching the irregular-shaped powdery-grains enclosing column 32.

The rotation drive section 18 includes a coupler 19 fitted to the stirring container 16 to detachably fix the stirring container 16, and a motor 21 that rotates the stirring container 16 fitted to the coupler 19, with a motor shaft being fixed to the coupler 19.

The stirring container 16 is formed substantially in a cylindrical shape as a whole, and has a stirring wall 17 having a flat surface extending along two directions, that is, a radial direction of the stirring container 16 and a direction of the axis of rotation, such that a side wall and a bottom of the stirring container 16 are depressed toward the axis of rotation and along the axis of rotation. The axis of rotation substantially matches with the axis of the stirring container 16, and the stirring wall 17 protrudes radially toward the axis of rotation, but does not go past the axis of rotation.

The suction flow channel 24 is inserted into the stirring container 16 through an opening 27, along the axis of rotation of the stirring container 16, and the suction port 23 is provided adjacent to the bottom of the stirring container 16 so as not to come in contact therewith. On the other hand, the discharge port 25 of the discharge flow channel 26 is inserted at a position away from the axis of rotation, so as to reach a position higher than the suction port 23, and higher than the stirring wall 17.

It is desired that an information processor having; an input device for inputting instructions from a user and data, a CPU that performs various kinds of arithmetic processing, a display device, various memories, and a communication device is provided in the electric circuit 20, as the control section that controls the device for capturing microbes or the like 10. The control section gives instructions to the pressure adjusting mechanism, the detaching machine, and the like in the device for capturing microbes or the like 10 and receives signals from these devices. The control section controls to determine a size or time of pressure applying in the flow channel by the pressure adjusting mechanism, and an amount, speed, or time of suction and discharge based on the structure of the flow channel, the structure of the irregular-shaped powdery-grains holding section (including the structure of the filter such as the pore diameter), the kind, grain size, or amount of the irregular-shaped powdery grains held by the irregular-shaped powdery-grains holding section, the amount or kind of the liquid, the kind or concentration of the target, and the purpose, time, or concentration factor (or dilution ratio) of the treatment.

FIG. 4 shows the stirring container 16 and the rotation drive section 18.

The backside of the stirring wall 17 has a slit-like gap portion 22 depressed radially and inward of the stirring container 16 and extending in the direction of the axis of rotation. An engagement plate 44 protruding radially toward the axis of rotation on an inner wall of the coupler 19 of the rotation drive section 18 is fitted to the gap portion 22, so that the stirring container 16 and the coupler 19 coaxially coupled with the motor 21 are coupled coaxially, thereby enabling to reliably transfer a rotation operation of the motor 21 to a rotation operation of the stirring container 16.

Figure 5:
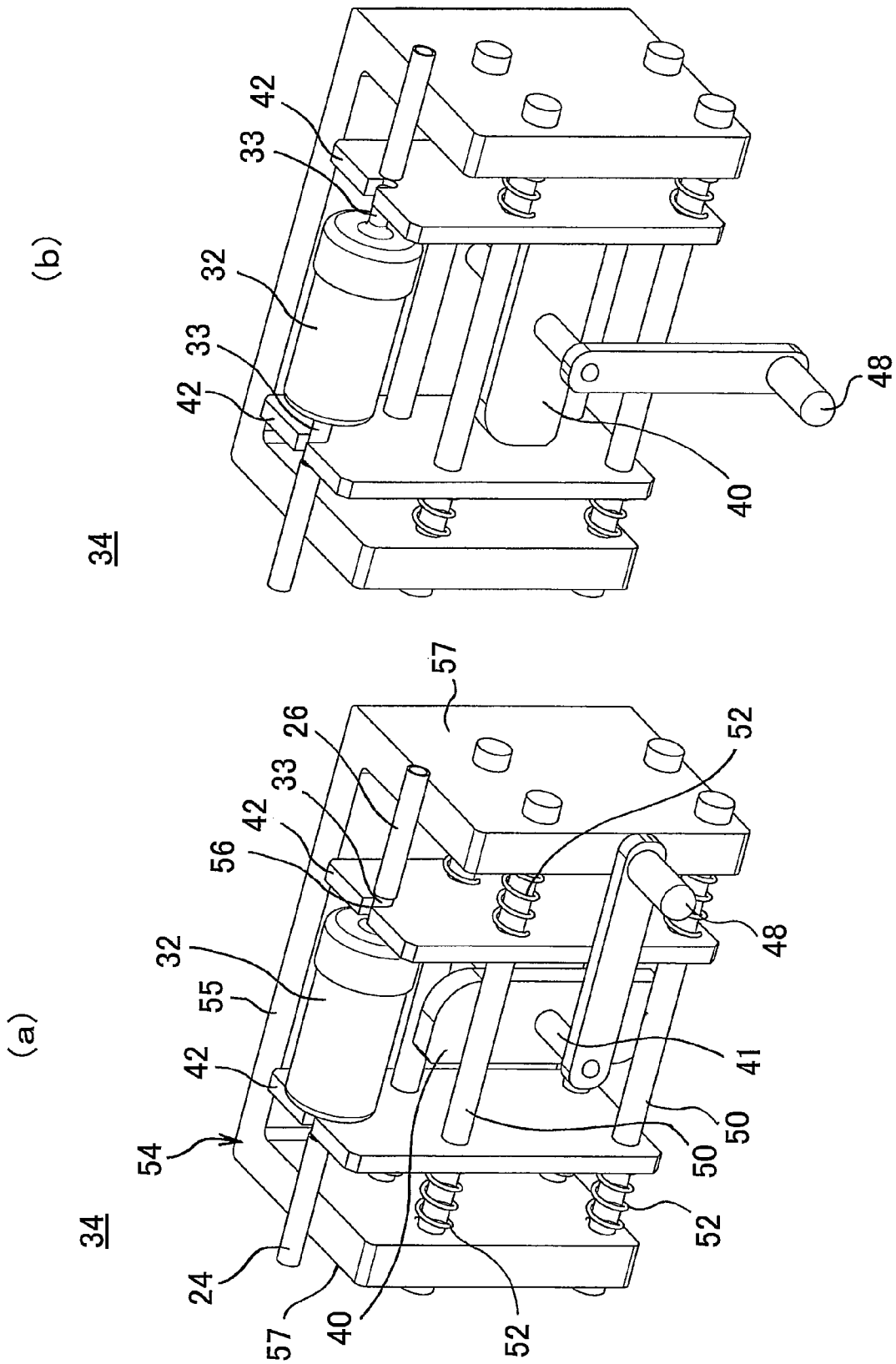
FIG. 5(a) is a perspective view showing a detaching machine in the device for capturing microbes or the like according to the second embodiment of the present invention.
FIG. 5(b) is a view similar to that of FIG. 5(a) but depicting a different operational mode.

FIG. 5 shows the column detaching machine 34 in detail. The column detaching machine 34 includes a frame 54 having a fitting side 55, which is fitted to the casing 12, and two opposite supporting sides 57 which are bent so as to be orthogonal to the fitting side 55 at the opposite ends of the fitting side 55, for supporting the suction flow channel 24 and the discharge flow channel 26 fitted with their ports inserted partway onto the connection short tubes 33 protrudingly provided at the opposite ends of the irregular-shaped powdery-grains enclosing column 32.

The two movable plates 42 each have a U-shaped groove 56 provided by cutting an upper edge thereof, and the grooves 56 contact with the connection short tubes 33 of the irregular-shaped powdery-grains enclosing column 32 to support the irregular-shaped powdery-grains enclosing column 32. The movable plates 42 are slidably provided along a shaft 50 penetrating the movable plates 42 and spanning between the supporting sides 57, and are urged so as to be pressed to the irregular-shaped powdery-grains enclosing column 32 by springs 52 provided so as to be sandwiched between the supporting sides 57 and the movable plates 42.

The cam 40 is provided so as to be sandwiched between the movable plates 42. The cam 40 is formed substantially in a rectangular plate-shape, in which a cam shaft 41 perpendicular to the flat surface is provided in the middle of the plate, and the cam shaft 41 is provided with a handle 48 for rotating the cam 40. A length of the cam 40 in a longitudinal direction is set to a range such that the two movable plates 42 can be separated fully apart so that the ports of the suction flow channel 24 and the discharge flow channel 26 can be detached from the connection short tubes 33, but the grooves 56 do not come off from the connection short tubes 33. The apexes of the cam 40 at the four corners are chamfered in a curved surface corresponding to the turning radius so as to smoothly come in contact with the movable plates 42.

FIG. 5 (*a*) shows a state in which the movable plates 42 are urged by the spring and pressed against the irregular-shaped powdery-grains enclosing column 32, and a force is not applied to the port of the discharge flow channel 26, that is, a state in which the irregular-shaped powdery-grains enclosing column 32 is fitted to the discharge flow channel 26 via the short tube 33. FIG. 5 (*b*) shows a state in which the movable plates 42 are pressed by the cam in a direction in which the movable plates are separated away from each other, and the discharge flow channel 26 is stripped away from the connection short tube 33 by the groove 56 in the movable plate 42, that is, a state in which the irregular-shaped powdery-grains enclosing column 32 is detached from the discharge flow channel 26.

Figure 6:
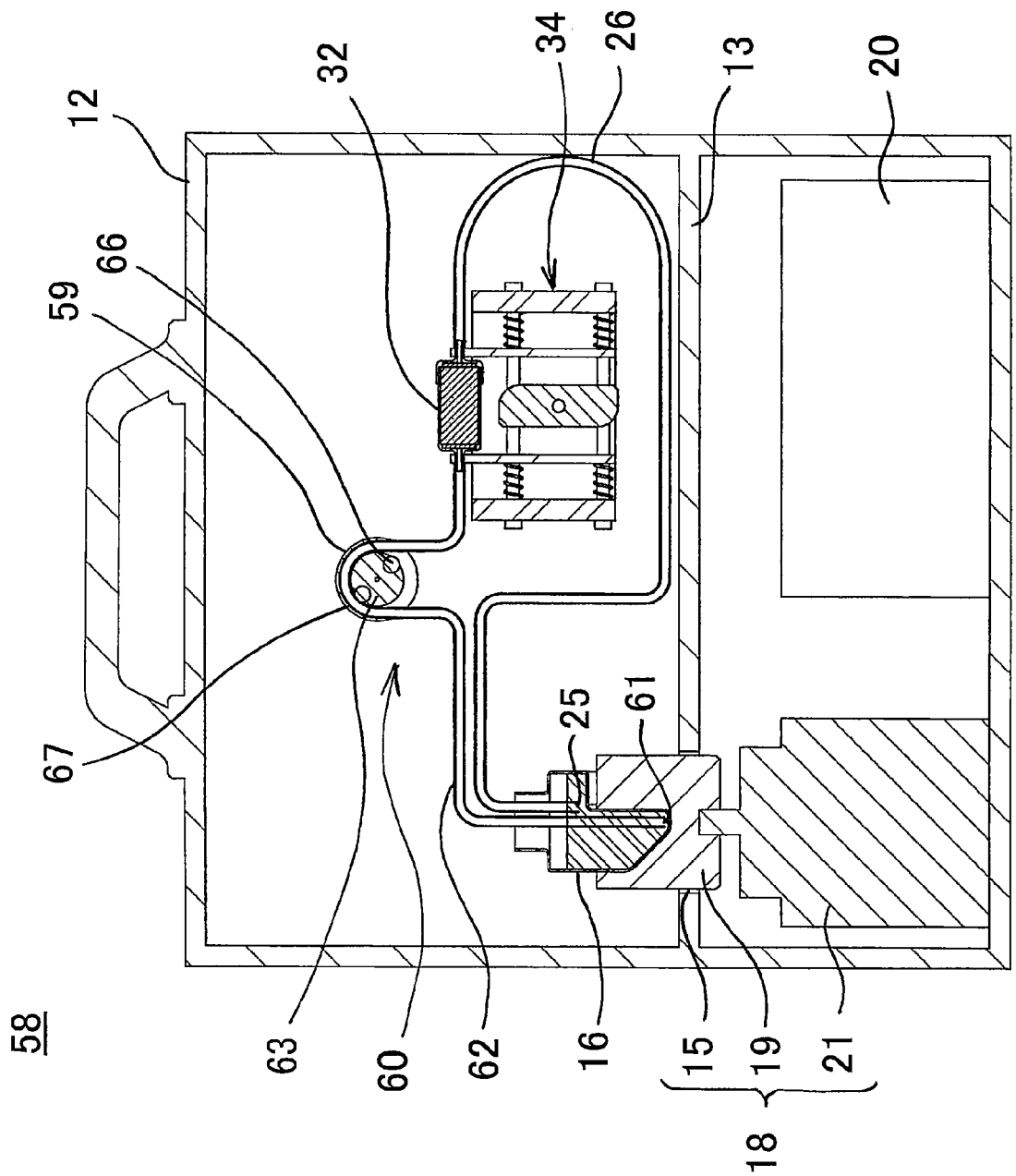
FIG. 6 is a sectional view showing a device for capturing microbes or the like according to a third embodiment of the present invention.

FIG. 6 shows a device for capturing microbes or the like 58 according to a third embodiment.

The device for capturing microbes or the like 58 is different from the device for capturing microbes or the like 10 according to the second embodiment in that a peristaltic pump is used instead of the bellows pump. Like reference symbols refer to like parts in FIG. 3, and detailed explanation thereof is omitted.

The device for capturing microbes or the like 58 has a microbes or the like capturing section 60 housed above the partition plate 13 provided in the casing 12. The microbes or the like capturing section 60 includes, as the flow channel, a suction flow channel 62 formed of an elastic resin such as fluorine resin rubber or silicone, inserted into the stirring container 16 and having one suction port 61 through which suction of a liquid is performed, and a discharge flow channel 26 inserted into the stirring container 16 and having one discharge port 25 through which discharge of the liquid is performed. A part of the suction flow channel 62 passes through a liquid feed section 59 for feeding the liquid therein in a suction direction by squeezing the suction flow channel 62.

The liquid feed section 59 has two openings through which the suction flow channel 62 passes, and further includes: a cylindrical frame 67 in which the suction flow channel 62 is housed inside between the openings, curved in a U-shape along an inner wall thereof; a roller 63 provided coaxially with the cylindrical frame 67 so as to have a space capable of housing the suction flow channel 62 between the inner wall of the cylindrical frame 67 and the roller 63, and rotated by a motor (not shown); and squeezing sections 66 provided in the roller 63 at two positions, on either side of a rotation shaft that rotates together with the roller 63, so as to protrude in a radial direction of the roller 63 and stick out more that than the radius of the roller 63, to squeeze the suction flow channel 62 housed in the cylindrical frame 67.

Figure 7:
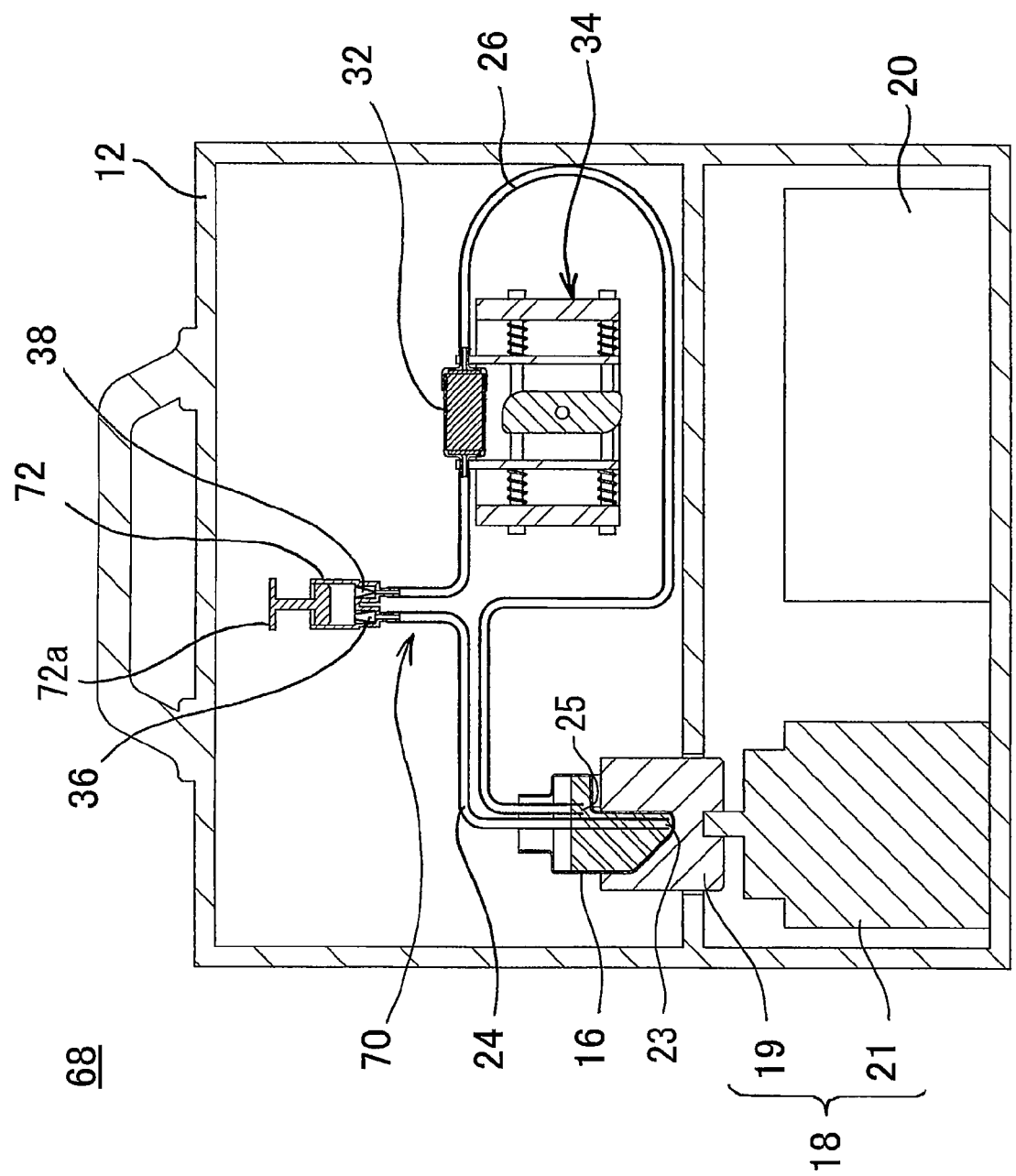
FIG. 7 is a sectional view showing a device for capturing microbes or the like according to a fourth embodiment of the present invention.

FIG. 7 shows a device for capturing microbes or the like 68 according to a fourth embodiment.

The device for capturing microbes or the like 68 is different from the device for capturing microbes or the like 10 according to the second embodiment in that a cylinder pump 72 is used instead of the bellows pump 30. Like reference symbols refer to like parts in FIG. 3, and explanation thereof is omitted.

The device for capturing microbes or the like 68 includes the casing 12 and a microbes or the like capturing section 70 housed above the partition plate 13 provided in the casing 12. In the cylinder pump 72, a piston 72*a* that slides in the cylinder moves vertically by the upward and downward movement of an upward/downward movement mechanism (not shown) using a motor and a ball screw mechanism, to suck a liquid via the suction port 23, and the liquid is discharged from the discharge port 25.

Subsequently, *Legionella* bacteria (*Legionella* bacteria) in water in a heat storage tank to be tested is concentrated for the purpose of performing a *Legionella* bacteria cultivation test by using the device for capturing microbes or the like 10 according to the second embodiment.

In step S21, for example, the device for capturing microbes or the like 10 according to the second embodiment is carried to the heat storage tank in which it is considered that the *Legionella* bacteria are suspended in the water. The suction port 23 of the suction flow channel 24 in the microbes or the like capturing section 14, and the discharge port 25 of the discharge flow channel 26, are extended to the outside of the casing 12 and inserted into the water in the heat storage tank, instead of the stirring container 16, and set, and the bellows pump 30 is operated for about 30 minutes to treat 5 liters of water.

In step S22, the irregular-shaped powdery-grains enclosing column 32 is detached from the microbes or the like capturing section 14.

In step S23, the irregular-shaped powdery grains 11 serving as a material for capturing microbes or the like are taken out from the irregular-shaped powdery-grains enclosing column 32, and placed in a container which is then filled with 0.5 ml of 0.1M HCl—KCl (ph2.2), and left for four minutes at 25° C.

In step S24, the irregular-shaped powdery grains 11 are stirred 10 times in a dissociation solution (eluate), and left to stand for 5 minutes, and the dissociation solution is collected.

In step S25, for example, the dissociation solution is diluted 10-fold in saline solution as required, and 100 μl of diluted solution is applied to a *Legionella* bacteria selective medium WYOα plate.

In step S26, culturing is performed for five to seven days at 37° C. while preventing drying out.

On the other hand, for comparison with the conventional technique, a procedure of a method using centrifugal separation according to Revised Guidelines for Control and Prevention of *Legionella* bacteria (Japan Environmental Sanitation Center, H11) is described below.

In step S31, as a case for where about the same treatment time is spent for the same water in the heat storage tank, 200 ml of water in the heat storage tank is placed into a sterile centrifuging tube, and the sterile centrifuging tube is loaded into a centrifuge to perform centrifugal separation at 6000 rpm at 4° C. for 20 minutes.

In step S32, 1 ml of precipitate is left and the supernatant is removed.

In step S33, 1 ml of 0.2M HCl—KCl (pH 2.2) is added and left to stand for 4 minutes at 25° C.

In step S34, 100 µl of precipitate is applied to the *Legionella* bacteria selective medium WYOα plate.

In step S35, culturing is performed for five to seven days at 37° C. while preventing drying out.

The results when the above-described treatment is applied to two types of different water A and B in the heat storage tank sampled from a separate heat storage tank are shown in FIG. 8.

It is assumed here that the "number of colonies" in FIG. 8 is viable bacteria counts in 0.1 ml. An "initial biomass concentration" is calculated by multiplying the "number of colonies" by a dilution ratio or a concentration factor, and indicates the viable bacteria counts present in 100 ml of water in the heat storage tank.

As shown in this experiment, according to the device for capturing microbes or the like 10 according to the second embodiment, a sensitivity of 47 times to 79 times that in the conventional cooling centrifuging method can be obtained from the number of colonies, and for calculation of the initial biomass concentration, the same results can be obtained in the method using the device according to the second embodiment and in the conventional cooling centrifuging method.

Figure 9:
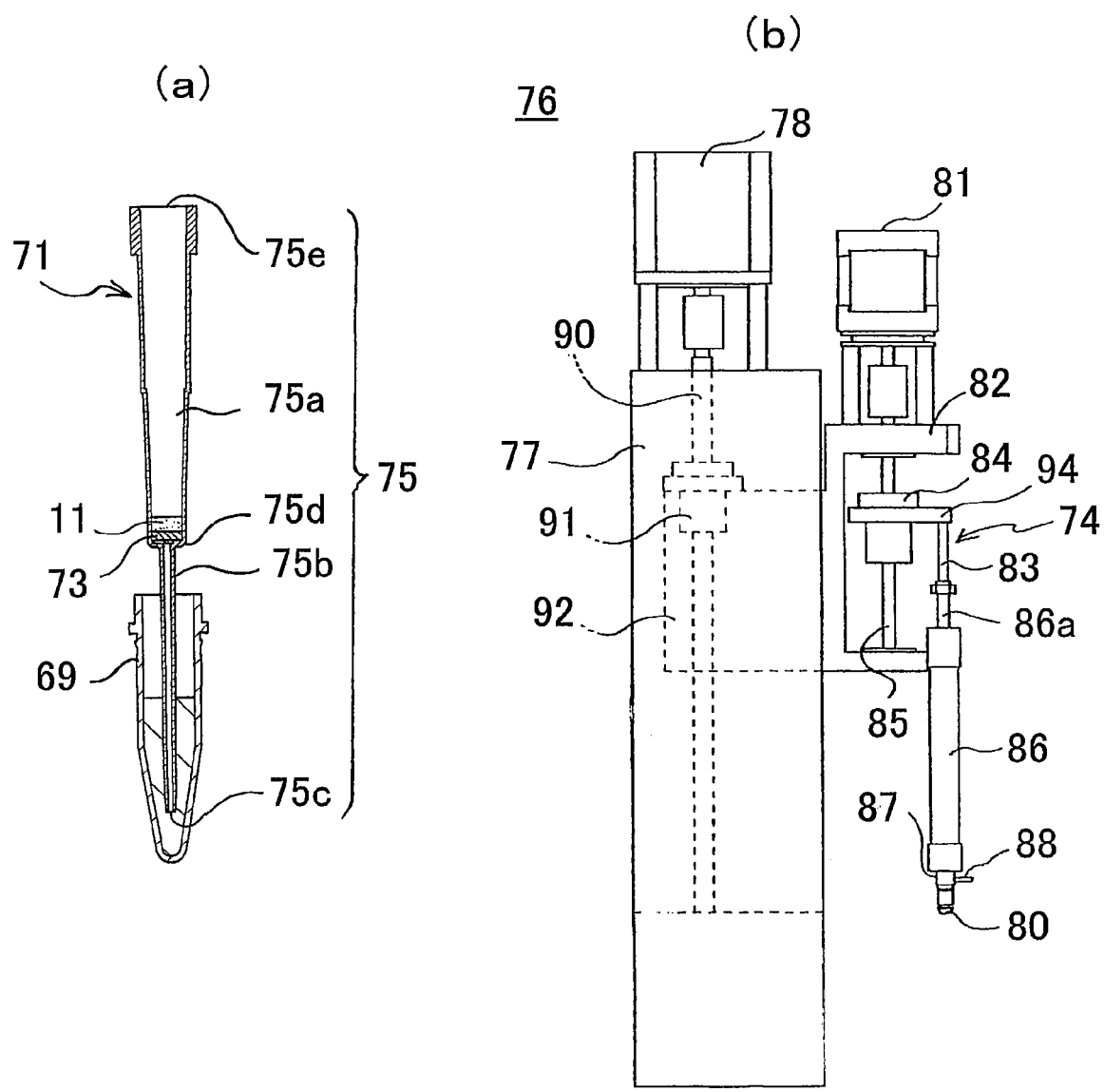
FIG. 9(a) is a sectional view showing a column tip of a device for capturing microbes or the like according to a fifth embodiment of the present invention.
FIG. 9(b) is a sectional view showing a column tip drive mechanism of the device for capturing microbes or the like according to the fifth embodiment of the present invention.

FIG. 9(*a*) shows a column tip 71 corresponding to the microbes or the like capturing section according to the fifth embodiment of the present invention, and FIG. 9(*b*) shows a column tip drive mechanism 76 that drives the column tip 71.

The column tip 71 includes: a tip-like container 75 having a large diameter tube 75*a* that stores the irregular-shaped powdery grains 11 serving as the material for capturing microbes or the like, a small diameter tube 75*b* provided with a port 75*c*, through which a liquid can flow in and out, at the tip thereof, a step portion 75*d* provided between the large diameter tube 75*a* and the small diameter tube 75*b*, and a fitting opening 75*e* to be fitted to an end of a nozzle 80 of the column tip drive mechanism 76; one filter 73 held so as to partition the large diameter tube 75*a* and the small diameter tube 75*b*, by using a step of the step portion 75*d*; and the irregular-shaped powdery grains 11 stored on the filter 73 in layers. For example, when the diameter of the large diameter tube 75*a* is 6 to 7 mm, the grain size of the irregular-shaped powdery grains 11 is 180 µm to 90 µm. When 40 mg of the irregular-shaped powdery grains 11 are stored on the filter 73, the thickness thereof becomes about 5 mm to 1 cm. The number of the powdery grains is about 25000.

The port 75*c* at the end of the small diameter tube 75*b* is inserted into a container 69 that stores the liquid to be treated.

The column tip drive mechanism 76 includes a nozzle head 74 having the nozzle 80. There is provided; a connecting section 87 that connects to a cylinder 86 provided just above the nozzle 80 and provided with a pipe line 88 that leads gas to a pressure sensor (not shown) for detecting pressure in the nozzle 80, the cylinder 86 connected to the nozzle 80 via the connecting section 87, a piston 86*a* that slides in the cylinder 86, and a rod 83 that drives the piston 86*a*. The rod 83 is fitted to a notch provided at an edge of a vertically movable drive plate 94 so as to hook a portion protruding toward a radial edge and having a larger diameter than that of the rod 83. The nozzle head 74 can move in the transverse direction, in other words, left/right direction in the drawing.

The drive plate 94 is connected to a nut 84 threaded onto a ball screw 85. The rod 83 is urged downward at all times by a spring provided 8 on the cylinder 86. Therefore, when moving upward, the rods 83 are raised by the respective nuts 84, while when moving downward, the rods 83 go down by the spring force, not by the respective nuts 84. The respective ball screws 85 are rotated by a motor 81 provided on a support member 82 having a U-shape in cross-section. Accordingly, the drive plate 94 and the rod 83 move vertically together.

A ball screw 90, a nut 91 threaded onto the ball screw 90, and a support body 92 having the support member 82 fitted to the nut 91 at one end, are housed in a case 77. A motor 78 that rotates the ball screw 90 is provided on the case 77. The nozzle 80 can move vertically by a vertical movement mechanism formed by these parts.

The column tip drive mechanism 76 is provided so as to be suspended from an upper side in a casing.

The capturing degree when colon *bacillus* serving as the microbes or the like are captured by using the column tip 71 serving as the microbes or the like capturing section, is compared between a case where the irregular-shaped powdery grains 11 are used as the material for capturing microbes or the like and a case where a simple pulverizable adsorptive resin material is used.

An experiment was performed for a case of the column tip 71 in which the irregular-shaped powdery grains 11 were stored in the tip-like container 75. The irregular-shaped powdery grains 11 were generated by drying a quaternary amine resin ground product (irregular-shaped) produced by Organo Corporation, having a grain size in a range of from 150 µm to 90 µm, for 10 minutes at 70° C. 40 mg of the dried irregular-shaped powdery grains 11 were stored and held in the tip-like container 75 to which the filter 73 was fitted, and used for capturing colon *bacillus*.

When the turbidity O.D.$_{660}$ of *Escherichia coli* in which the colon *bacillus* was suspended was 0.505, the *Escherichia coli* suspension was stored in the container 69. The column tip 71 was fitted to the nozzle 80 of the column tip drive mechanism 76 at the fitting opening 75*e*, and the port 75*c* of the end of the column tip 71 was inserted into the container 69 to repeat suction and discharge five times. Then, the colon *bacillus* in the *Escherichia coli* were adsorbed to the surface of the irregular-shaped powdery grains 11 and captured, and a residual liquid including uncaptured colon *bacillus* was discharged into the container 69 via the port 75*c*.

When the turbidity of the residual liquid was measured by light having a wavelength of 660 nm, a turbidity O.D.$_{660}$=0.195 was obtained.

FIG. 10(*a*) shows a number of irregular-shaped powdery grains 11 formed of strongly basic gel-type ion exchange resin (Model No. IRA410JCL by Organo Corporation). FIG. 10(*b*) shows an image obtained by an electronic microscope in an enlarged state in which a number of colon *bacillus* are adsorbed to one irregular-shaped powdery grain 11. FIG. 10(*c*) shows an image of the irregular-shaped powdery grain 11 obtained by an electronic microscope in a further enlarged state. The plurality of dots seen on the surface of the irregular-shaped powdery grain 11 is the adsorbed colon *bacillus*. When it is assumed that the size of the colon *bacillus* is 180 to 90 µM, the number of irregular-shaped powdery grains 11 per 20 mg is about 12000, and the surface area thereof when the irregular-shaped powdery grains 11 are converted to a sphere becomes about 7.1 cm$^2$. If it is assumed that the size of the colon *bacillus* is approximated to 1 to 1.5 µm long and 2 to 6 µm wide, and biomasses can be spread on the powdery grains, it is considered that the entire number of colon *bacillus* in the liquid is from $9 \times 10^7$ to $3.2 \times 10^8$ in the experiment. Therefore, approximately $9 \times 10^7/12000$ to $3.2 \times 10^8/12000$ colon *bacillus* can be adsorbed per one powdery grain.

Next measurement was performed inside the column tip 71, by performing the treatment using an unpulverized pulverizable resin material instead of the irregular-shaped powdery grains 11 serving as the material for capturing microbes or the like.

First, an experiment was performed for a case where the unpulverized pulverizable resin material was stored in the tip-like container 75. Conditions the same as those described above were set for a resin material, which was a CH08P quaternary amine resin unpulverized product (spherical shape) produced by Mitsubishi Chemical Corporation, having a grain diameter of 150 to 75 µm. That is, the grain diameter was classified into 150 to 90 µm and the resin material was dried at 70° C. for 10 minutes. 40 mg of the dried pulverizable resin material was stored and held in a tip-like container 75$f$ in which the filter 73 was fitted, and was used for capturing colon *bacillus*.

When the turbidity O.D.$_{660}$ of *Escherichia coli* was 0.505 as in the same case as described above, the *Escherichia coli* suspension was stored in the container 69. The tip-like container 75 was fitted to the nozzle 80 of the column tip drive mechanism 76 at the fitting opening 75$e$, and the port 75$c$ of the end of the tip-like container 75 was inserted into the container 69 to repeat suction and discharge five times. Then, colon *bacillus* in the *Escherichia coli* were captured by the surface of the pulverizable resin material, and a residual liquid containing uncaptured colon *bacillus* was discharged into the container 69 via the port 75$c$.

When the turbidity of the residual liquid was measured by light having a wavelength of 660 nm, a turbidity O.D.$_{660}$=0.328 was obtained. That is, it is seen that the capturing degree by the column tip 71 is larger than the case of using the unpulverized pulverizable resin material.

Subsequently, a method of storing microbes or the like according to the sixth embodiment will be explained with reference to FIG. 11.

A method of storing *Legionella* bacteria contained in a specimen extracted from an actual test body (water in the heat storage tank) will be explained, by applying the powdery grains 11 for capturing *Legionella* bacteria (for example, *Legionella pneumophila* species) to the specimen. Grain size of the powdery grains 11 was classified in a range from 90 to 250 µm.

Figure 11:
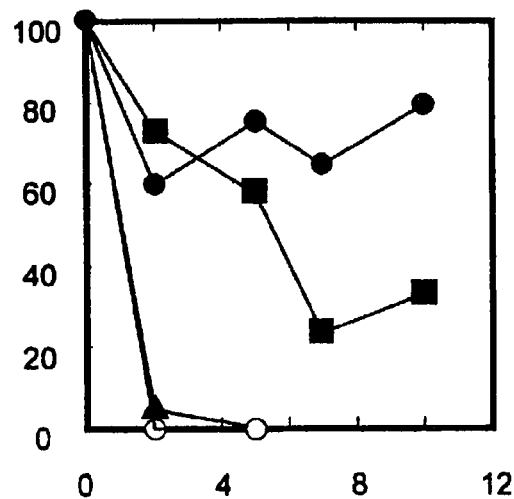
FIG. 11(a) is a diagram showing results obtained by applying a method of storing microbes or the like according to a sixth embodiment of the present invention.
FIG. 11(b) is another diagram showing results obtained by applying a method of storing microbes or the like according to the sixth embodiment of the present invention.

The graph shown in FIG. 11 ($a$) shows the number of colonies when a solution with *Legionella pneumophila* species SG1 serotype in an amount of about $10^3$ to $10^4$ cfu/ml in a saline solution condition or with 100 mg of the powdery grains 11 added thereto, was stored at 4° C. or 37° C., and after 0 to 10 days, was cultured for five days in a BCYEα agar medium (BD). Moreover the table shown in FIG. 11 ($b$) shows a ratio of the number of colonies when the number of colonies on the 0th day is designated as 100% plotted as the survival rate. In the conventional *Legionella* test, after a specimen is sent to a test facility by cool delivery service, the specimen is concentrated by the centrifugation method or filter method described above, and detected by culturing or nucleic acid amplification (LAMP method).

As shown in FIG. 11($a$) and FIG. 11($b$), *Legionella pneumophila* species SG1 serotype cannot be stored at room temperature. On the other hand, even when *Legionella pneumophila* species SG1 serotype is stored at 4° C., in a storage solution only containing the saline solution as in the conventional case, a survival rate of 60% or less is shown on the fifth day, and the survival rate rapidly decreases. On the other hand, when the powdery grains 11 according to the sixth embodiment are used, a survival rate of about 80% is held even after 10 days. A target can be sampled and stored easily in a state being adsorbed to the powdery grains 11, by using the powdery grains 11 according to the sixth embodiment, without using a large-scale device. Therefore, the target is concentrated at a site and the concentrate is sent in a state of being adsorbed to the powdery grains 11 to thereby facilitate the concentration operation and increase the sensitivity in detection.

Concentration, collection, and detection treatments of *Legionella* bacteria will be explained next. An example in which; the powdery grains 11 classified in a range of grain size of 90 to 250 µm, the device for capturing microbes or the like 58 according to the third embodiment, and the irregular-shaped powdery-grains enclosing column, are used for concentration and collection of *Legionella* bacteria, and culturing, immunochromatography, and nucleic acid amplification are respectively used for detection of *Legionella* bacteria is explained, as compared with the results of the centrifugal separation method.

The roller 63 of the peristaltic pump of the device for capturing microbes or the like 58 to be used for concentration and collection of *Legionella* bacteria is rotated by a stepping motor, and the number of revolutions thereof can be adjusted between 40 to 150 rpm. A silicone tube (AS ONE Corporation) having an inner diameter of 5 mm and an external diameter of 9 mm or a flexible PVC tube (Sanyo Chemical Industries Ltd.) having an inner diameter of 6 mm and an external diameter of 9 mm is used for the peristaltic pump.

As the irregular-shaped powdery-grains enclosing column 32, a filter having a diameter of 12 mm was used for outdoor purposes, and a filter having a diameter of 8 mm was used for indoor purposes. It was considered that pore diameters of these filters were about 10 µm.

The treatment of *Legionella* bacteria includes a concentration process in step S41 and a detection process in step S43.

In the concentration process in step S41, the irregular-shaped powdery-grains enclosing column 32 is attached to the device for capturing microbes or the like 58, and the pump is driven for the length of time corresponding to the capacity thereof. For example, when it is used for outdoor purposes, because the sample is in an amount of from 5 to 10 liters, 200 mg of the powdery grains 11 are enclosed so as to be placed between the filters having a diameter of 12 mm to perform the concentration treatment for 30 to 60 minutes. Water in the heat storage tank at four locations of SY, YJ, YA and CK was used as an actual specimen.

When used for indoor purposes, because the sample is in an amount of about 0.5 liters, 100 mg of the powdery grains 11 are enclosed in the irregular-shaped powdery-grains enclosing column 32 so as to be placed between the filters having a diameter of 8 mm and the device is driven for 15 to 30 minutes.

In the collection process in step S42, the irregular-shaped powdery-grains enclosing column 32 is collected, and the powdery grains are stirred slowly, for example, 20 times in 250 µl or 500 µl of an eluate by using a syringe. The syringe is inserted into a lower part of the irregular-shaped powdery-grains enclosing column 32 and left for five minutes, and the eluate is shifted into a 1.5 mL tube. In the case where an HCl treatment is performed, the grains are soaked in 1 mL of HCl solution for four minutes before an elution operation and the HCl solution is discarded to perform the elution operation. The kind of the eluate is determined depending on the detection method in the next detection process.

For example, in the detection process in step S43, when culturing is used, 1M KPB is used as the eluate in step S42. In this case, the eluate is used directly as a culture medium, or the eluate is applied to the WYOα agar medium (Eiken Chemical Co., Ltd., E-MR70) or the like.

In the detection step in step S43, in the case where detection by the immunochromatography method is to be performed, as the eluate in step S42, 3M TB buffer solution of 3M in an amount of 250 μl to 500 μl is placed into a 1 mL syringe, and the syringe is inserted into the irregular-shaped powdery-grains enclosing column 32 to perform stirring. Thereafter, 100 μl of a buffer for spreading out of 1M KPB is mixed therein. Agglomeration of the bacteria with iron can be released by the mixing. The mixed solution 100 μl was applied to an immunochromatographic test strip, and the degree of color development after 15 minutes was recorded. A colored solution was judged positive, and an uncolored solution was judged negative. The immunochromatographic test strip was for a *Legionella pneumophila* species SG1 serotype.

In the detection process in step S43, in the case where detection is performed by nucleic acid amplification according to the PCR method and an electrophoretic profile, metal such as iron oxide and metal ions are mixed in a water sample in the heat storage tank, which tends to inhibit PCR. Therefore an amplification operation needs to be performed after performing a nucleic acid extraction operation to purify the sample, by simultaneously performing removal of metal ions and dissolution of bacteria by using alkali solution (for example, see Annual Report Vol. 15, 2000 by Niigata Prefectural Institute of Public Health and Environmental Sciences).

On the other hand, for a comparison purpose, the concentration method using the cooling centrifuging method described in Revised Guidelines for Control and Prevention of *Legionella* bacteria (March, 1999) was performed. In this method, 200 mL of sample was sampled and 50 mL was taken out in a centrifuging tube, and decanted slowly after being subjected to coolentrifuging at 600 rpm (the centrifugal force G is not disclosed) for 20 minutes. The sediment was suspended in 1 mL of sterile distilled water, and 1 mL of HCl/KCl (pH 2.2) of 0.2 M was added thereto and left to stand for 4 minutes. Thereafter, 100 μL was applied to a WYOα medium, and cultured for 5 to 7 days at 37° C., while preventing drying out.

The results of the above treatment are shown in FIGS. 12, 13, and 14.

In the concentration process for outdoor purposes, the concentration operation was directly performed at a site by using a concentration device from a heat storage tank CK. When detection was performed by the immunochromatography method, in the immunochromatographic test strip to which 100 μl of a concentrate was applied, a line was slightly detected after 5 minutes of development, and a clear line was confirmed after 15 minutes.

FIG. 12 (*a*) shows the results obtained by concentrating and culturing; water YJ in the heat storage tank, and a sample cultured in water in the heat storage tank and added with *Legionella pneumophila* species SG1 serotype, according to the cooling centrifuging method. FIG. 12 (*b*) shows rate of adsorption to the powdery grains 11 calculated based on a difference in the results obtained by concentrating and culturing a liquid having passed through the irregular-shaped powdery-grains enclosing column 32 at the time of concentrating 5 liters of the sample by using the device for capturing microbes or the like 58 according to the third embodiment of the present invention, according to the cooling centrifuging method.

Moreover, FIG. 12 (*c*) shows the results obtained by concentrating samples from the heat storage tanks at four locations by using the device for capturing microbes or the like according to the third embodiment of the present invention, and performing detection using the immunochromatography method, culturing, and the PCR method. Furthermore, the results obtained by a cooling centrifuging and concentration method are also shown for comparison. Concentration rates in this case are respectively 10000 times. The same culture detection results are obtained by using the device or method for capturing microbes or the like according to the third embodiment, and by using the cooling centrifuging and concentration method. In the immunochromatography method, there is a detection limit of $10^2$ cfu/ml of the concentrate from *Legionella pneumophila* species SG1 serotype, for the purpose of calculation. However, because only the SG1 serotype is detected, a positive result is not likely to be given as compared to the culture method for detecting the entire *Legionella* group.

Next, FIG. 13 shows the results for when the device for capturing microbes or the like 58 according to the third embodiment is used for indoor purposes.

Indoors, the amount of specimen for transporting the sample is limited. Therefore the concentration efficiency was increased by circulating a specimen of about 500 mL using the peristaltic pump. The concentration operation was performed by flowing at respective flow rates of speed 1 and speed 3 of the peristaltic pump from 500 mL of water YJ in the heat storage tank to which the cultured *Legionella* group, the *Legionella pneumophila* species, and the SG1 serotype were added. It took 7 minutes and 5.5 minutes, respectively, to concentrate 500 mL of water at speed 1 and speed 3 by one flow (from the suction port 61 to the discharge port 25). The number of colonies and initial concentration per culture plate are shown in FIG. 13 (*a*) as results obtained by performing the concentration operation, designating twice the time as 2 cycles and four times the time as 4 cycles (cycle: from the suction port 61 to the discharge port 25) in a circulating type, and at this time, concentrating and culturing the liquid having passed through the irregular-shaped powdery-grains enclosing column 32 according to the cooling centrifuging and concentration method. FIG. 13 (*b*) shows adsorption rates calculated based on respective culture results with respect to the control. The concentration efficiency can be comparatively increased by extending the circulation time based on these results.

FIG. 14 shows the culture results by using the device or method for capturing microbes or the like for outdoor and indoor purposes, and the results obtained by the cooling centrifuging method. In FIG. 14, the number of colonies in brackets indicates the number of contaminated colonies, "0" in the column "No." indicates the results by the cooling centrifuging and concentration method and "1" to "4" indicate the results obtained by using the device for capturing microbes or the like 58 according to the third embodiment of the present invention.

From the results, it is seen that the HCl treatment is not required so long as the device for capturing microbes or the like 58 or the method for capturing microbes or the like according to the third embodiment of the present invention is used. It is considered that this is due to the property of the powdery grains 11 such that it does not adsorb a large number of biomasses and the surface of the powdery grains 11 locally indicate acidity.

From the results described above, the following is shown. That is, the device and method for capturing microbes or the like using the powdery grains 11 according to the embodiments of the present invention could be applied to the culture method. In the case of an outdoor sample, the operation for concentrating the sample from 5 liters or 10 liters to 10000 times to 20000 times was possible. Capturing efficiency of the outdoor sample was 50% or higher by driving the pump for 30 minutes to 60 minutes. In the case of the indoor sample, the operation for concentrating the sample from 500 mL to 1000 times could be performed. Adsorption rate of the indoor sample was 80% or higher by circulating the sample for 15 to 30 minutes. The device and method for capturing microbes or the like according to the embodiments of the present invention indicate the same concentration efficiency as that in the method in the Guidelines, and in the indoor sample, the detection level could be decreased at a level of concentration of 10 to 20 times.

As described above, according to the device or method for capturing microbes or the like according to the respective embodiments, the concentration operation can be performed not in a laboratory, but in a place where there is the sample to be tested, without using a large-scale device. Therefore, the sample to be tested need not be transported. Furthermore, the concentration operation in a large capacity (500 mL or more), which is difficult to be performed by a centrifuging operation or a filtration operation, can be easily performed, and requires only minimal labor. Moreover, the device or method for capturing microbes or the like can be directly connected to a detection method requiring high density concentration such as the immunochromatography method, which is difficult to be performed by the centrifuging operation or the filtration operation. Furthermore, a simple operation is possible by a person other than a tester who has received training as a researcher or the like.

Even when the sample is to be transported, the sample containing the target such as microbes can be stored with a high survival rate by using the powdery grains according to the respective embodiments, and hence, highly accurate detection can be performed in a laboratory.

The respective embodiments described above are specifically explained for better understanding of the present invention, and are not for limiting other embodiments. Therefore, the embodiments can be modified within a range not changing the scope of the present invention. For example, in the embodiments, production and treatment of the irregular-shaped powdery grains serving as the material for capturing microbes or the like is performed for mainly three types of ion exchange resins. However, not only other pulverizable adsorbent resins for example other ion exchange resins, but also pulverizable chelate resins and a pulverizable adsorbent materials can be used.

In the above embodiments, the irregular-shaped powdery-grains enclosing column 32 is mainly provided on the downstream side of the bellows pump, the liquid feed section of the peristaltic pump, and the cylinder pump. However, the irregular-shaped powdery-grains enclosing column 32 can be provided on an upstream side thereof. Moreover a device provided with only one of these pumps or nozzles has been explained. However, a plurality of pumps or nozzles can be provided and arranged in the same device or these can be arranged in parallel. Furthermore the treatment of Legionella bacteria has been mainly explained. However, the present invention is applicable to the treatment of other bacteria, protozoa, cells, and the like other than the treatment of the Legionella bacteria. The present invention can be also applied to a case of capturing genetic materials such as DNA, oligonucleotide, and RNA, immune substances, protein, saccharides or the like. In addition, the numerical values, frequencies, shapes, numbers, and amounts used in the above explanation are not limited to these cases. Moreover, the reagents and substances described above indicate only an example, and other reagents and substances can be used.

INDUSTRIAL APPLICABILITY

The present invention is used for performing treatments such as extraction, analysis, and testing of immune substances such as antibodies and antigens, genetic materials (DNA, RNA, mRNA, oligonucleotide, and the like), biological polymers such as protein and hormonal substances, and other useful materials such as healthcare products, by capturing a target of microbes or the like such as bacteria, protozoa, body tissue, cells, and viruses. Moreover, the present invention is used in medical services, examination, diagnosis, healing, research, quantitative determination, qualitative analysis, and measurement in which separation, extraction, and concentration of a minor amount of targets of microbes or the like such as cells are performed automatically and reliably.

The invention claimed is:

1. A material for capturing microbes, which comprises irregular-shaped powdery grains made of a pulverizable adsorbent resin and distributed in a grain size range from 30 μm to 100 μm, and which can be suspended in a liquid, and adsorb or bond to a target including any one of microbes selected from bacteria, fungus, and protozoa contained in a liquid.

2. A material for capturing microbes according to claim 1, wherein said pulverizable adsorbent resin includes a pulverizable ion exchange resin, a pulverizable chelate resin, or a pulverizable absorbent.

\* \* \* \* \*